(12) United States Patent
Cuenoud et al.

(10) Patent No.: US 6,670,468 B1
(45) Date of Patent: Dec. 30, 2003

(54) 2'-SUBSTITUTED NUCLEOSIDES AND OLIGONUCLEOTIDE DERIVATIVES

(75) Inventors: Bernard Cuenoud, Horsham (GB); Karl-Heinz Altmann, Reinach (CH); Pierre Martin, Rheinfelden (CH); Heinz Ernst Moser, Horsham (GB)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/753,943

(22) Filed: Jan. 3, 2001

Related U.S. Application Data

(63) Continuation of application No. 09/194,844, filed as application No. PCT/EP97/02738 on May 27, 1997, now abandoned.

(30) Foreign Application Priority Data

Jun. 6, 1996 (CH) .............................................. 1432/96

(51) Int. Cl.[7] .......................... C07H 21/04; C12P 19/34
(52) U.S. Cl. ...................................... 536/25.3; 435/91.1
(58) Field of Search ........................... 514/44; 536/23.1, 536/24.5, 24.3, 24.33, 24.31, 25.3; 435/6, 91.1

(56) References Cited

U.S. PATENT DOCUMENTS

| | | | |
|---|---|---|---|
| 5,571,902 A | * | 11/1996 | Ravikumar et al. |
| 5,744,362 A | * | 4/1998 | Monia et al. |
| 5,750,673 A | | 5/1998 | Martin ...................... 536/26.1 |

FOREIGN PATENT DOCUMENTS

| | | |
|---|---|---|
| CA | 2123241 | 11/1994 |
| DE | 41 10 085 | 10/1992 |
| EP | 0 679 657 | 11/1995 |
| WO | WO 91/06556 | 5/1991 |
| WO | WO 91/15499 | 10/1991 |
| WO | 92/03568 | 3/1992 |
| WO | 95/03568 | 3/1992 |
| WO | 93/07883 | 4/1993 |
| WO | 93/13121 | 7/1993 |
| WO | 93/17717 | 9/1993 |
| WO | 94/02501 | 2/1994 |
| WO | 95/06659 | 3/1995 |
| WO | WO 95/32980 | * 12/1995 |

OTHER PUBLICATIONS

Beaucage et al., Tetrahedron Report No. 309, vol. 48, No. 12, pp. 2223–2311 (1991).
Cohen J. et al., Scientific American, The New Genetic Medicines, pp. 50–55 (1994).
Crooke et al, International ISBN 3–540–58890–6, Medical Intelligence Unit, Therapeutic Applications of Oligonucleotides, R. G. Landes Company, Austin.
De Mesmaecker et al., Current Opinion in Structural Biology, vol. 5, pp. 343–355 (1995).
Douglas M. et al., Pergamon, Bioorg. & Medicinal Chemistry Letters, vol. 4, No. 8, pp. 995–1000 (1994).
Inoue et al., Nucleic Acids Research, vol. 15, No. 15, pp. 6131–6148 (1987).
Iribarren A., et al., Biochemistry, Proc. Natl. Acad. Sci., USA, vol. 87, pp. 7747–7751 (1990).
Keller et al., Helvetica Chimica Acta., vol. 76, pp. 884–892 (1993).
Keller et al., Nucleic Acids Research, vol. 21, No. 19, pp. 4499–4505 (1993).
Lesnik. et al., Biochemistry, vol. 32, pp. 7832–7838 (1993).
Manoharan M. et al., Tetrahedron Letters, vol. 32, No. 49. pp. 7171–7174 (1991).
Martin P., Helvetica Chimica Acta, vol. 78, pp. 486–504 (1995).
Plum G. et al., Annu. Rev. Biophys. Biomol. Struct., vol. 24, pp. 319–350 (1995).
Stull R. et al., Phamaceutical Research, vol. 12, No. 4, pp. 465–483 (1995).
Abstract 92–332937 (DE 4110 085, Nov. 15, 1993).
Copy of International Search Report.

* cited by examiner

*Primary Examiner*—Sean McGarry
*Assistant Examiner*—Janet L. Epps-Ford
(74) *Attorney, Agent, or Firm*—George B. Dohmann

(57) ABSTRACT

The invention relates to an oligonucleotide derivative which comprises at least one nucleoside building block of the formula (I)

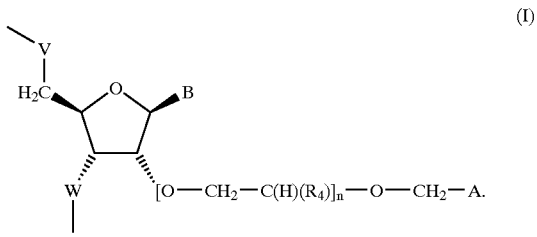

The invention furthermore relates to nucleoside building blocks, intermediates and processes for preparing the oligonucleotide derivatives and the nucleoside building blocks. The invention also relates to pharmaceutical compositions and to uses of the oligonucleotide derivatives and the nucleoside building blocks.

4 Claims, No Drawings

SEQUENCE LISTING

<160> NUMBER OF SEQ ID NOS: 22

<210> SEQ ID NO 1
<211> LENGTH: 20
<212> TYPE: RNA
<213> ORGANISM: Homo sapiens

<400> SEQUENCE: 1
aaugcauguc acaggcggga                    20

<210> SEQ ID NO 2

```
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: 1-20
<223> OTHER INFORMATION: at least one modified sugar residue

<400> SEQUENCE: 2
tcccgcctgt gacatgcatt                                                   20

<210> SEQ ID NO 3
<211> LENGTH: 15
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: 5
<223> OTHER INFORMATION: 2'-substituted sugar

<400> SEQUENCE: 3
tttttctctc tctct                                                        15

<210> SEQ ID NO 4
<211> LENGTH: 15
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: 5, 7, 9, 11 and 13
<223> OTHER INFORMATION: 2'-substituted sugar

<400> SEQUENCE: 4
tttttctctc tctct                                                        15

<210> SEQ ID NO 5
<211> LENGTH: 16
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: 1, 7, 9 and 15
<223> OTHER INFORMATION: 2'-substituted sugar

<400> SEQUENCE: 5
tccaggtgtc cgcatc                                                       16

<210> SEQ ID NO 6
<211> LENGTH: 15
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: 1-5
<223> OTHER INFORMATION: 2'-substituted sugar

<400> SEQUENCE: 6
tttttctctc tctct                                                        15
```

```
<210> SEQ ID NO 7
<211> LENGTH: 15
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: 5-14
<223> OTHER INFORMATION: 2'-substituted sugar
<220> FEATURE:
<221> NAME/KEY: modified_base
<222> LOCATION: 6, 8, 10, 12, 14
<223> OTHER INFORMATION: 5-methyl cytosine

<400> SEQUENCE: 7 ttttctctc tctct                                              15

<210> SEQ ID NO 8
<211> LENGTH: 15
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: 1-14
<223> OTHER INFORMATION: 2'-substituted sugar
<220> FEATURE:
<221> NAME/KEY: modified_base
<222> LOCATION: 6, 8, 10, 12, 14
<223> OTHER INFORMATION: 5-methyl cytosine

<400> SEQUENCE: 8 ttttctctc tctct                                              15

<210> SEQ ID NO 9
<211> LENGTH: 15
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: 5-14
<223> OTHER INFORMATION: 2'-substituted sugar
<220> FEATURE:
<221> NAME/KEY: modified_base
<222> LOCATION: 6, 8, 10, 12, 14
<223> OTHER INFORMATION: 5-methyl cytosine

<400> SEQUENCE: 9 ttttctctc tctct                                              15

<210> SEQ ID NO 10
<211> LENGTH: 15
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: 11
<223> OTHER INFORMATION: 2'-substituted sugar

<400> SEQUENCE: 10
agagagagag aaaaa                                             15

<210> SEQ ID NO 11
<211> LENGTH: 15
<212> TYPE: DNA
```

```
<213> ORGANISM: Artificial Sequence
<220> FEATURE:
<223> OTHER INFORMATION: synthesized
<220> FEATURE:
<221> NAME/KEY: misc_feature
<222> LOCATION: 3, 5, 7, 9, 11
<223> OTHER INFORMATION: 2'-substituted sugar

<400> SEQUENCE: 11
agagagagag aaaaa                                                    15

<210> SEQ ID NO 12
<211> LENGTH: 15
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: 11-14
<223> OTHER INFORMATION: 2'-substituted sugar

<400> SEQUENCE: 12
agagagagag aaaaa                                                    15

<210> SEQ ID NO 13
<211> LENGTH: 15
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: 2-11
<223> OTHER INFORMATION: 2'-substituted sugar

<400> SEQUENCE: 13
agagagagag aaaaa                                                    15

<210> SEQ ID NO 14
<211> LENGTH: 13
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: 4, 6, 12
<223> OTHER INFORMATION: 2'-substituted sugar

<400> SEQUENCE: 14
aggtgtccgc atc                                                      13

<210> SEQ ID NO 15
<211> LENGTH: 16
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: 13-15
<223> OTHER INFORMATION: 2'-substituted sugar

<400> SEQUENCE: 15
tccaggtgtc cgtttc                                                   16

<210> SEQ ID NO 16
<211> LENGTH: 21
```

```
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: none
<223> OTHER INFORMATION: Target DNA

<400> SEQUENCE: 16
gctaaaaaga gagagagatc g                                              21

<210> SEQ ID NO 17
<211> LENGTH: 21
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: none
<223> OTHER INFORMATION: Opposite strand of target DNA seq. ID 16

<400> SEQUENCE: 17
cgatctctct ctcttttag c                                               21

<210> SEQ ID NO 18
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: 1-20
<223> OTHER INFORMATION: phosphorothioate backbone
<220> FEATURE:
<221> NAME/KEY: misc_feature
<222> LOCATION: 2, 4, 15, 17, 19
<223> OTHER INFORMATION: 2'-substituted sugar

<400> SEQUENCE: 18
tcccgcctgt gacatgcatt                                                20

<210> SEQ ID NO 19
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: 6-15
<223> OTHER INFORMATION: phosphorothioate backbone
<220> FEATURE:
<221> NAME/KEY: misc_feature
<222> LOCATION: 1-5 and 15-19
<223> OTHER INFORMATION: 2'-substituted sugar

<400> SEQUENCE: 19
tcccgcctgt gacatgcatt                                                20

<210> SEQ ID NO 20
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: 1-20
```

```
<223> OTHER INFORMATION: phosphorothioate backbone
<220> FEATURE:
<221> NAME/KEY: misc_feature
<222> LOCATION: 1-5 and 15-19
<223> OTHER INFORMATION: 2'-substituted sugar

<400> SEQUENCE: 20
tcccgcctgt gacatgcatt                                              20

<210> SEQ ID NO 21
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: 6-15
<223> OTHER INFORMATION: phosphorothioate backbone
<220> FEATURE:
<221> NAME/KEY: misc_feature
<222> LOCATION: 1-5 and 15-19
<223> OTHER INFORMATION: 2'-substituted sugar

<400> SEQUENCE: 21
tcccgcctgt gacatgcatt                                              20

<210> SEQ ID NO 22
<211> LENGTH: 20
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: 1-20
<223> OTHER INFORMATION: phosphorothioate backbone
<220> FEATURE:
<221> NAME/KEY: misc_feature
<222> LOCATION: 1-5 and 15-19
<223> OTHER INFORMATION: 2'-substituted sugar

<400> SEQUENCE: 22
tcccgcctgt gacatgcatt                                              20
```

2'-SUBSTITUTED NUCLEOSIDES AND OLIGONUCLEOTIDE DERIVATIVES

This is a continuation of Ser. No. 09/194,844, filed May 14, 1999 now abandoned, which is a 371 of application No. PCT/EP97/02738 filed May 27, 1997.

AREA OF INVENTION

The present invention relates to an oligonucleotide derivative which comprises at least one nucleoside building block which is substituted at the 2' position. The invention furthermore relates to intermediates, to processes for preparing the oligonucleotide derivatives, to their uses and to pharmaceutical compositions.

BACKGROUND TO THE INVENTION

As chemotherapeutic agents, oligonucleotides and oligonucleotide derivatives open up effective possibilities for treating many different pathological states which are characterized by expression of a protein or an RNA molecule, for example hyperplastic or neoplastic changes in a cell or a tissue. They can exert their effect, in particular, by way of the so-colled antisense mechanism. Oligonucleotides and oligonu employed in this manner are consequently termed "antisense oligonucleotides". Alternatively, an oligonucleotide can exert its effect by way of the so-called triplex mechanism. Such oligonucleotides and oligonucleotide derivatives are termed "triplex-forming oligonucleotides".

For an oligonucleotide or oligonucleotide derivative to be advantageously suitable for use as an antisense oligonucleotide or as a triplex-forming oligonucleotide, it should possess specific properties. Thus, for example, it should have adequate binding affinity for a target nucleic acid, possess adequate resistance to nucleases, in particular towards endogenous nucleases, and, in the case of exerting an effect by way of an antisense mechanism, completely or partially inhibit the translation of a target DNA by means of the formation of a hybrid and subsequent cleavage of the target RNA strand by endogenous nucleases, such as RNAse H, or by means of the formation of a hybrid and subsequent complete or partial inhibition of the ribosomal translation process (so-called translation arrest), or, in the case of exerting an effect by way of a triplex mechanism, the transcription of a particular double-stranded gene segment or DNA segment should be completely or partially inhibited by means of the formation of a triple helix. Furthermore, the oligonucleotide or oligonucleotide derivative should be taken up to an adequate extent by the cell to be treated, should exert an effect which is as sequence-specific as possible, and possess adequate bioavailability (cf., for example, S. T. Crooke, "Therapeutic Applications of Oligonucleotides", R. G. Landes Company Publisher (1995); Plum, G. E., Annu. Rev. Biophys. Biomol. Struct. 24 (1995), 319–350; Cohen, J. S. et al., Sci. Am. (1994), 50–55; Stull, R. A. et al., Pharm. Res. 12 (1995), 465–483).

In order to obtain oligonucleotides or oligonucleotide derivatives which possess one or more of the abovementioned properties, substitutions have, for example, been performed on the nucleoside building blocks or the internucleosidic bonds from which the oligonucleotides and oligonucleotide derivatives are assembled.

There is a particular need for additional or improved oligonucleotide derivatives in the antisense field or the triplex field.

Ready industrial accessibility to such oligonucleotide derivatives, for example a simple or economic preparation method, would be a further advantage.

An object of the present invention is consequently to make available additional or improved oligonucleotide derivatives which, particularly in relation to their use as antisense oligonucleotides or triplex-forming oligonucleotides, have advantageous properties with regard to one or more of the following criteria:

binding affinity
resistance to nucleases
sequence-specific effect
inhibition or modulation of expression
uptake by the cell
bioavailability.

Another object of the present invention is to make available compounds which ensure ready industrial accessibility to oligonucleotide derivatives according to the invention.

A further object lies in the provision of an oligonucleotide derivative or a pharmaceutical which can be used in a mammalian subject, including man, to treat, in particular, pathological states which are characterized by the expression of a protein or an RNA molecule.

SUMMARY OF THE INVENTION

The invention provides an oligonucleotide derivative which comprises at least one nucleoside building block which has a substituent of the type described below at the 2'-O position.

The invention also provides a nucleoside compound which can be used as an intermediate in the preparation of the novel oligonucleotide derivatives.

The invention also provides processes for preparing the novel oligonucleotide derivatives and processes for preparing the nucleoside compounds and also other intermediates which are used.

The invention furthermore provides a pharmaceutical composition which comprises the novel oligonucleotide derivatives and also a use of these oligonucleotide derivatives for therapeutic treatment, for modulating the expression of a protein or an RNA molecule, and in diagnostic methods.

The invention also provides the use of the novel nucleoside compounds in pharmaceutical compositions and for therapeutic treatment.

PRECISE DESCRIPTION OF THE INVENTION

Surprisingly, it has been ascertained that one or more of the above-described objects is/are achieved by a novel oligonucleotide derivative according to the present invention.

Consequently, the invention provides an oligonucleotide derivative which comprises at least one nucleoside building block of the formula I

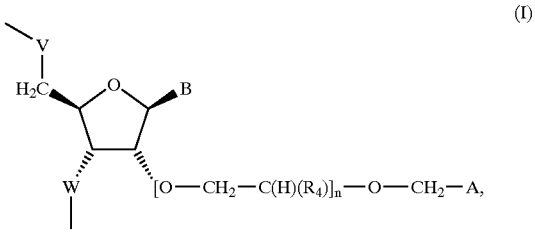

in which
A is a radical of the formula —C(H)(R$_3$)—N(R$_1$)(R$_2$), in which $R_1$ and $R_2$ are, independently of each other
H,
$C_1$–$C_{10}$alkyl,
a radical of the formula II

in which each X is, in each case independently of each other, O or $N(R_6)$, $R_5$ and $R_6$ are, in each case independently of each other, H, $C_1$–$C_{10}$ alkyl, amino-$C_2$–$C_{10}$alkyl, N-mono-$C_1$–$C_{10}$alkylamino-$C_2$–$C_{10}$alkyl or N,N-di-$C_1$–$C_{10}$alkylamino-$C_2$–$C_{10}$alkyl, and m is an integer from 1 up to and including 3, amino-$C_3$–$C_{10}$alkyl, N-mono-$C_1$–$C_{10}$alkylamino-$C_3$–$C_{10}$alkyl, or N,N-di-$C_1$–$C_{10}$alkylamino-$C_3$–$C_{10}$alkyl; or in which —$N(R_1)(R_2)$ are together a radical of the formula (III),

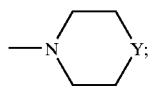

in which Y is O, S, $SO_2$ or $N(R_7)$, and $R_7$ is H or —$CH_3$;
$R_3$ is H, —$CH_3$, —$CH_2CH_3$, —$CH_2OH$ or —$CH_2$—O—$C_1$–$C_4$alkyl; or
A is a radical of the formula (IVa) or (IVb)

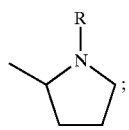

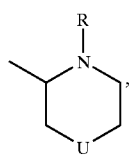

in which R, independently, has the meaning of $R_1$ or $R_2$, and U is O or $CH_2$;
$R_4$ is H, —$CH_3$, —$CH_2CH_3$, —$CH_2OH$ or —$CH_2$—O—$C_1$–$C_4$alkyl;
n is 0, 1 or 2;
B is the radical of a nucleic acid base; and
V and W are, independently of each other, the same or different radicals of an internucleosidic bridging group or are a terminal radical;
or a salt thereof;
where those compounds are excepted in which, in the radical A, two heteroatoms are linked to the same carbon atom.

In a further embodiment of the radical of formula (III) Y is SO.

The expression "oligonucleotide derivative" is familiar to the skilled person and will only be explained here for the sake of completeness. Within the context of the present invention, the expression "oligonucleotide derivative" denotes, in particular, a derivatized oligonucleotide. An oligonucleotide per se is preferably an oligomer which consists of a sequence of natural nucleoside building blocks which are connected to each other by way of natural internucleosidic bridging groups. A natural nucleoside as such preferably consists of a sugar, in particular a β-D-erythropentofuranose, in particular β-D-ribose, together with a natural nucleic acid base which is linked to it in the P position. Within the context of the present invention, nucleic acid base preferably denotes a base which, in relation to a naturally occurring nucleoside, is capable of forming Watson-Crick base pairing (for antisense oligonucleotides) or of forming Hoogsteen or reverse Hoogsteen base pairing (for triplex-forming oligonucleotides). Examples of natural nucleic acid bases are adenine, guanine, cytosine, thymine and uracil and also other bases with which the skilled person is familiar. In an oligonucleotide, a natural internucleosidic bridging group, in particular a phosphodiester group connects the individual nucleosides to each other, in each case by way of the 3' and 5' positions. In this connection, "natural" preferably means that the corresponding compounds or residues occur in nature and are accessible by isolation from corresponding natural products or by means of chemical synthesis. Consequently, those compounds or residues which are not regarded as being natural are termed "derivatives" or "analogues". Within the context of this invention, the expression "oligonucleotide derivative" therefore preferably denotes an oligonucleotide which encompasses a nucleoside building block of the formula (I) at at least one position. Furthermore, such an oligonucleotide derivative can be structurally modified, as compared with a corresponding natural oligonucleotide, at at least one further position (this can relate to the sugar or the base of another nucleoside building block, or to an internucleosidic bridging group). Thus, for example, another internucleosidic bridging group can be present in place of the naturally occurring phosphodiester bond; another linkage, for example a 2'-5' linkage, can be present in place of the natural internucleosidic 3'-5' linkage of nucleoside building blocks; a base analogue which is likewise capable of hybridizing with the strand of a target nucleic acid within the sense of Watson-Crick, Hoogsteen or reverse Hoogsteen base pairing can be present in place of a natural base; or the sugar residue can be derivatized at different positions, for example the 2'-position or the 6'-position. However, an oligonucleotide derivative can also comprise, in place of at least one nucleoside building block, at least one nucleoside analogue which encompasses a non-sugar backbone to which a nucleic acid base is linked.

Derivatized oligonucleotides, nucleosides, internucleosidic bridging groups and analogues have been described (cf., for example, De Mesmaeker, A. et al., Curr. Op. Struct. Biol. 5 (1995), 343–355; Sanghvi Y. S. et al., (Ed.), "Carbohydrate Modifications in Antisense Research", ACS Symposium Series 580 (1994); S. T. Crooke, "Therapeutic Applications of Oligonucleotides", R. G. Landes Company Publisher (1995); the entire content of these publications is hereby incorporated by reference).

A preferred embodiment of the present invention relates to a novel oligonucleotide derivative which comprises at least one abovementioned nucleoside building block of the formula (I), in which
A is a radical of the formula —$C(H)(R_3)$—$N(R_1)(R_2)$, in which
$R_1$ and $R_2$ are, independently of each other, H, $C_1$–$C_5$alkyl, amino-$C_2$–$C_5$alkyl, N-mono-$C_1$–$C_3$alkylamino-$C_2$–$C_5$alkyl, N,N-di-$C_1$–$C_3$alkylamino-$C_2$–$C_5$alkyl or a radical of the formula II

in which X is O or $N(R_6)$, $R_5$ and $R_6$ are, independently of each other, H, $C_1$–$C_3$alkyl, amino- $C_2$–$C_3$alkyl, N-mono-$C_1$–$C_3$alkylamino-$C_2$–$C_5$alkyl or N, N-di-$C_1$–$C_3$alkylamino-$C_2$–$C_5$-alkyl, and m is 1; and where $R_3$ has the said meanings and is, in particular, H.

$R_1$ and $R_2$ are preferably, independently of each other, H, methyl, ethyl, aminoethyl, aminopropyl, N-monomethylaminoethyl, N-monomethylaminopropyl, N-monoethylaminoethyl, N-monoethylaminopropyl, N,N-dimethylaminoethyl, N,N-dimethylaminopropyl, N,N-diethylaminoethyl, N,N-diethylaminopropyl, or a radical of the formula II

in which X is O or N($R_6$), $R_5$ and $R_6$ are, independently of each other, H, methyl, ethyl or propyl, and m is 1.

In addition, $R_1$ and $R_2$ are preferably, independently of each other, H, methyl, ethyl, aminoethyl, N-monomethylaminoethyl, N-monoethylaminoethyl, N,N-dimethylaminoethyl or N,N-diethylaminoethyl, and $R_1$ and $R_2$ are particularly preferably, independently of each other, H, methyl or ethyl.

Very particular preference is given to oligonucleotide derivatives according to the invention in which $R_1$ and $R_2$ are in each case H, or $R_1$ and $R_2$ are in each case methyl, or one of the substituents $R_1$ and $R_2$ is H and the other is methyl.

Oligonucleotide derivatives according to the invention are also preferred in which $R_1$ and $R_2$ are in each case methyl, or one of the substituents $R_1$ and $R_2$ is H and the other is methyl.

In the oligonucleotide derivatives according to the invention, including the said preferences, R3 and $R_4$ are, independently of each other, preferably H, —$CH_3$, —$CH_2OH$ or —$CH_2$—O—$CH_3$.

Preference is given to oligonucleotide derivatives according to the invention, including the said preferences, in which n is 0.

Oligonucleotide derivatives according to the invention are particularly advantageous in which n is 0 and A is a radical of the formula —C(H)($R_3$)—N($R_1$)($R_2$), in which $R_3$ is H, and $R_1$ and $R_2$ are defined as above, including the said preferences.

An oligonucleotide derivative according to the invention is furthermore preferred which comprises at least one said nucleoside building block of the formula (I), in which A is a radical of the formula —C(H)($R_3$)—N($R_1$)($R_2$), in which —N($R_1$)($R_2$) is a radical of the said formula (III), with, particularly preferably, Y being N($R_7$) and $R_7$ being H or, particularly preferably, being —$CH_3$; in this context, n is preferably 0, $R_3$ is preferably H.

Another preferred embodiment relates to an oligonucleotide derivative according to the invention which comprises a said nucleoside building block of the formula (I) in which A is a radical of the said formula (IVa) with, particularly preferably, R being H or $C_1$–$C_{10}$alkyl, in particular H; in this context, n is preferably 0.

Within the context of the present invention, a nucleic acid base B (or B', see below) is understood as being, in particular, natural nucleic acid bases and known analogues (cf., for example, Accounts of Chem. Res. 28 (1955), pp. 366–374; Sanghvi, Y. S. in: Antisense Research and Applications, Crooke, S. T. and Lebleu, B. (Ed.), CRC Press, Boca Raton (1993), pp. 273–288; the entire content of these publications is hereby incorporated by reference). As is familiar to the skilled person, nucleic acid bases B (or B', see below) can exist in tautomeric forms depending on the ambient conditions. According to the invention, such tautomeric forms are also encompassed by the oligonucleotide derivatives according to the invention, including the preferred embodiments.

The invention furthermore relates to oligonucleotide derivatives according to the invention, including the said preferences, in which B is a radical of the formula (V1) to (V14)

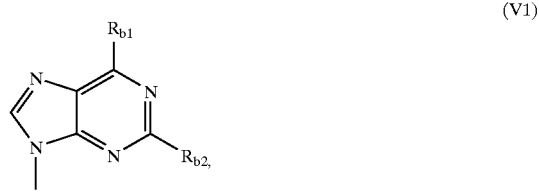

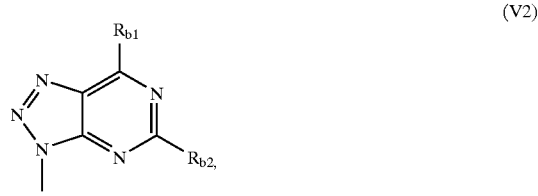

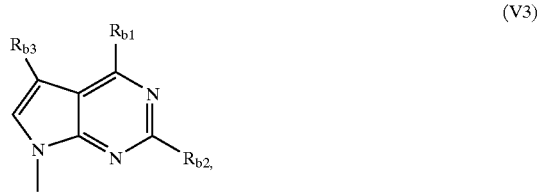

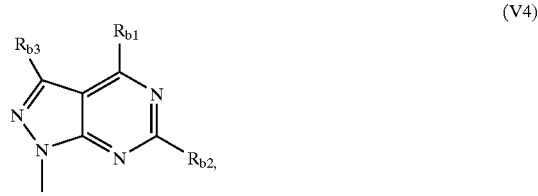

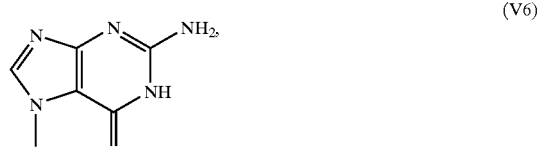

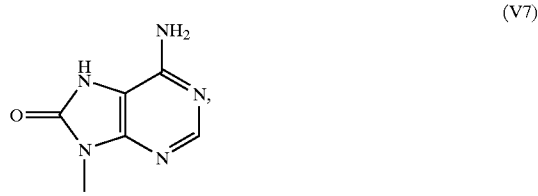

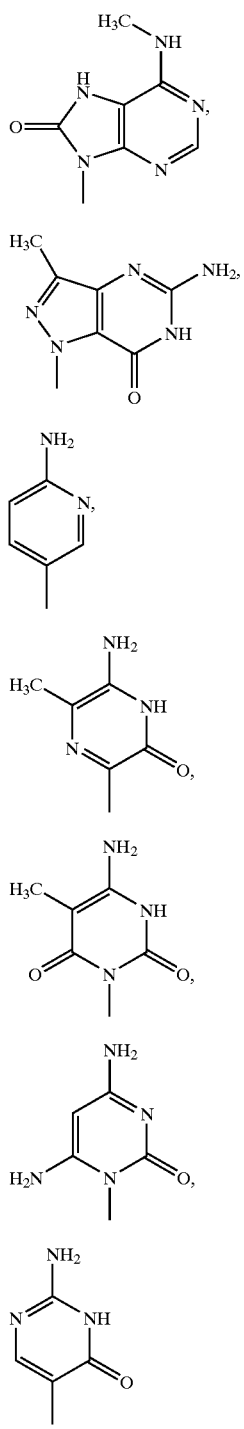

in which
R$_{b1}$ is —NH$_2$, —SH or —OH;
R$_{b2}$ is H, —NH$_2$ or —OH; and
R$_{b3}$ is H, Br, I, —CN, —C≡C—CH$_3$, —C(O)NH$_2$ or —CH$_3$;
R$_{b4}$ is —NH$_2$ or —OH; and
R$_{b5}$ is H, F, Br, I, —CN, —C≡C—CH$_3$, —C(O)NH$_2$ or —CH$_3$.

Preference is given to an oligonucleotide derivative according to the invention in which B is a radical of the formula (V1), (V2), (V3), (V4) or (V5)

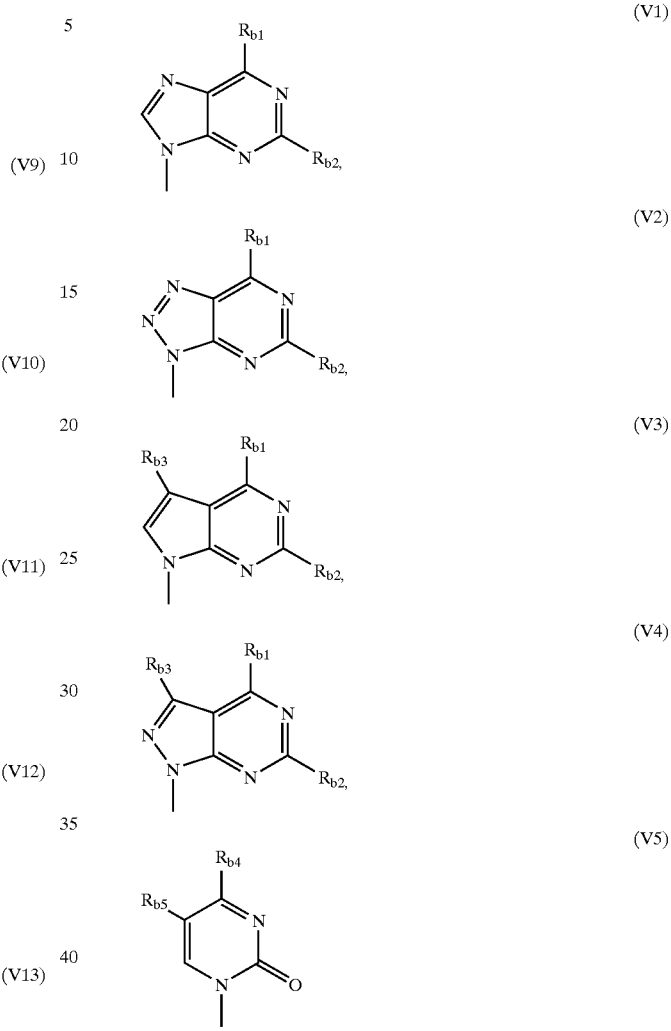

in which
R$_{b1}$ is —NH$_2$, —SH or —OH;
R$_{b2}$ is H, —NH$_2$ or —OH; and
R$_{b3}$ is H, Br, I, —CN, —C≡C—CH$_3$, —C(O)NH$_2$ or —CH$_3$;
R$_{b4}$ is —NH$_2$ or —OH; and
R$_{b5}$ is H, F, Br, I, —CN, —C≡C—CH$_3$, —C(O)NH$_2$ or —CH$_3$.

In a preferred embodiment of an oligonucleotide derivative according to the invention, B is a radical of the formula (V1) or (V5)

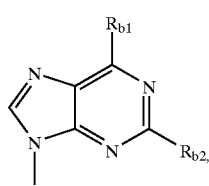

-continued

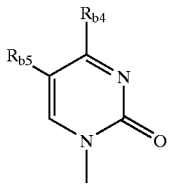

(V5)

in which

R_{b1} is —NH$_2$, —SH or —OH;

R_{b2} is H, —NH$_2$ or —OH;

R_{b4} is —NH$_2$ or —OH; and

R_{b5} is H, F, Br, I, —CN, —C≡C—CH$_3$, —C(O)NH$_2$ or —CH$_3$.

In particular, B is selected from the group of the following radicals: xanthine, hypoxanthine, adenine, 2-aminoadenine, guanine, 6-thioguanine, uracil, thymine, cytosine, 5-methylcytosine, 5-propynyluracil, 5-fluorouracil and 5-propynylcytosine.

In the oligonucleotide derivatives according to the invention, including the said preferences, V and W in particular constitute, independently of each other, the radical of an internucleosidic bridging group. Such internucleosidic bridging groups, and methods for preparing them and introducing them into nucleoside building blocks, oligonucleotides and oligonucleotide derivatives have been described in large numbers and are familiar to the skilled person, as mentioned above. Customary internucleosidic bridging groups are suitable within the context of the present invention.

Preferably, V and W, as radicals of an internucleosidic bridging group, are selected, independently of each other, from the following group: 5'-O—P(O)(OH)—O-3' (phosphodiester), 5'-O—P(O)(SH)—O-3' (phosphorothioate), 5'-O—P(S)(SH)—O-3' (phosphodithioate), 5'-O—P(O)(CH$_3$)—O-3' (methylphosphonate), 5'-O—P(O) (NH—R$_7$)—O-3' (phosphoamidate) in which R$_7$ is C$_1$–C$_3$alkyl, 5'-O—P(O) (OR$_8$)—O-3' (phosphotriester) in which R$_8$ is C$_1$–C$_3$alkyl, 5-O—S(O)$_2$—CH$_2$-3' (sulfonate), 5'-O—S(O)$_2$—NH-3' (sulfamate), 5'-NH—S(O)—CH$_2$-3'(sulfonamide), 5'-CH$_2$—S(O)$_2$—CH$_2$-3' (sulfone), 5'O—S(O)—O-3' (sulfite), 5'CH$_2$—S(O)—CH$_2$-3' (sulfoxide), 5'CH$_2$—S—CH$_2$-3' (sulfide), 5'-O—CH$_2$—O-3' (formacetal), 5'-S—CH$_2$—O-3' (3'-thioformacetal), 5'O—CH$_2$—S-3' (5'-thioformacetal), 5'-CH$_2$—CH$_2$—S-3' (thioether), 5'-CH$_2$—NH—O-3' (hydroxylamine), 5'CH$_2$—N(CH$_3$)—O-3' (methylene(methylimino)), 5'-CH$_2$—O—N(CH$_3$)-3' (methyleneoxy(methylimino)), 5'-O—C(O)—NH-3' (5'-N-carbamate), 5'-CH$_2$—C(O)—NH-3' (amide), 5'-NH—C(O)—CH$_2$-3' (amide II), 5'-CH$_2$—NH—C(O)-3' (amide III) and 5'-C(O)—NH—CH$_2$-3' (amide IV), and the tautomeric forms thereof.

The 5' and 3' orientation of the said radicals V and W, as an internucleosidic bridging bond, may be clarified as follows:

When V is a radical 5'-CH$_2$—C(O)—NH-3' (amide), the corresponding nucleoside building block of the above-defined formula (I) has the following structure (I. 1):

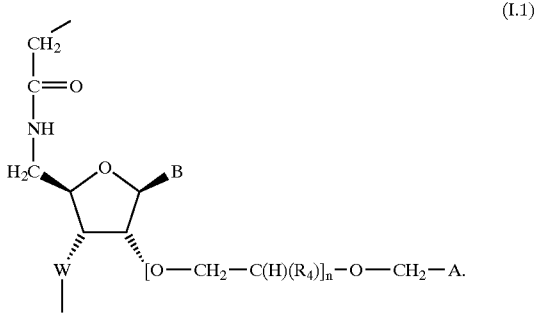

(I.1)

When W is a radical 5'-CH$_2$—C(O)—NH-3' (amide), the corresponding nucleoside building block of the above-defined formula (I) has the following structure (I. 2):

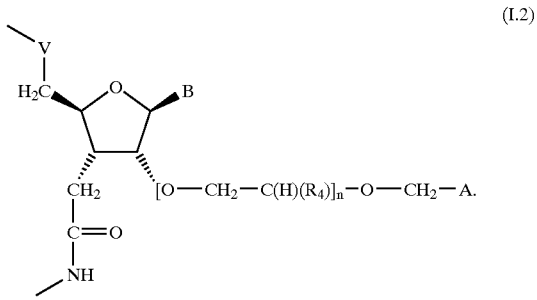

(I.2)

Some of the said radicals of internucleosidic bridging groups can exist in different tautomeric forms, depending, inter alia, on the solvent and on the degree of ionization of ionizable groups. Thus, for example, the bridging group in a phosphorothioate [O—(P—SH)(=O)—O] can be tautomerized to [O—(P—OH)(=S)—O], with the more stable form depending, inter alia, on the solvent and the ionization state. Within the context of the present invention, the term "oligonucleotide derivative" also encompasses those tautomeric forms which are familiar to the skilled person.

Particularly preferably, V and W, as the radical of an internucleosidic bridging group, are selected, independently, from the following group: 5'-O—P(O)(OH)—O-3' (phosphodiester), 5'-O—P(O)(SH)—O-3' (phosphorothioate) and 5'-CH$_2$—C(O)—NH-3' (amide).

In particular, one of the radicals V or W, as the radical of an internucleosidic bridging group, is 5'-O—P(O)(OH)—O-3' (phosphodiester) and the other radical is 5'-O—P(O) (SH)—O-3' (phosphorothioate).

V and W are also preferably, as the radical of an internucleosidic bridging group, in each case 5'-O—P(O)(OH)—O-3' (phosphodiester) or in each case 5'-O—P(O)(SH)—O-3' (phosphorothioate).

As the terminal radical in formula (I), V and W are preferably, independently of each other, —OH, —NH$_2$, or a protected hydroxyl group or amino group. It is furthermore preferred for V, as a terminal radical, to be —OH, —NH₂ or a protected hydroxyl group or amino group, and W to be —OH or —NH₂. In particular, V and W, as a terminal radical, are in each case —OH or —NH₂. Otherwise, the abovementioned preferences for oligonucleotide derivatives according to the invention are preferred in this case as well.

In addition to at least one nucleoside building block of the formula I, the oligonucleotide derivatives according to the invention can comprise further natural or derivatized nucleoside building blocks.

A natural nucleoside building block consists of a pentofuranosyl radical, preferably a ribosyl radical, in particular a β-D-ribosyl radical or a β-D-2'-deoxyribosyl radical with a nucleic acid base linked to it, and of a radical of a phosphodiester bond as the radical of an internucleosidic bridging group. Such a natural nucleoside building block has the following formula VI and/or VI* (here, and in that which follows, the structural difference between nucleoside building blocks whose formula is labelled with an asterisk "*" and those whose formula is not marked by an asterisk lies in the position of the linking point of the internucleosidic bridging group on the sugar or sugar analogue of the nucleoside):

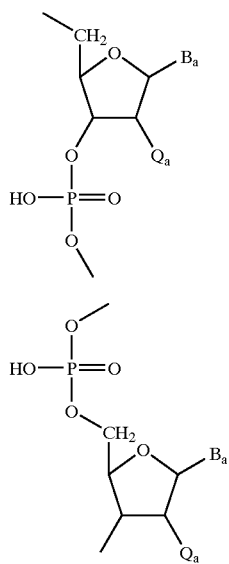

(VI)

(VI*)

in which $Q_a$ is H or —OH; and $B_a$ is the radical of a nucleic acid base, selected, in particular, from thymine, uracil, 5-propynyluracil, cytosine, 5-methylcytosine, 5-propynylcytosine, adenine, 2-aminoadenine and guanine.

It is known that the replacement, in an oligonucleotide or oligonucleotide derivative, of one or more phosphodiester bonds with a derivatized internucleosidic bridging bond, preferably with one of the abovementioned internucleosidic bridging bonds, confers advantageous properties on the oligonucleotide derivative, in particular with regard to resistance to nucleases or binding affinity for a target nucleic acid. It is furthermore known that the insertion into an oligonucleotide of particular substituents (other than those which form part of the subject-matter of the present invention), in particular at the 2' position, likewise confers advantageous properties, in particular with regard to resistance to nucleases or binding affinity for a target nucleic acid (cf., for example, Martin, P., Helv. Chem. Acta, 78 (1995), 486–504; Lesnik, E. A. et al., Biochemistry 32 (1993), 7832–7838; Inoue, H. et al., Nucl. Acids Res. 15 (1987), 6131–6148; Douglas, M. E. et al., Bioorg. Med. Chem. Let. 4 (1994), 995–1000; Manoharan, M. et al., Tet. Lett. 32 (1991), 7171–7174; Keller, T. H. et al., Helv. Chimia Acta 76 (1993), 884–892; Iribarren, A. M. et al., Proc. Nat. Acad. Sci. USA 87 (1990), 7747–7751; International Applications WO 94/02501; WO 93/13121; WO 95/16696; WO 91/06556; WO 93/07883; WO 91/15499; WO 92/03568; DE 91–4110085; WO 95/06659).

The following are therefore preferred examples of further nucleoside building blocks for oligonucleotide derivatives according to the invention:

Nucleoside building blocks which differ from those of the formula VI or VI* in that, in place of the substituents $Q_a$ a substituent Q is present which is H, —OH, —SCH₃, —F, —N₃, —CN, —OCN, —OCH₃, —O(CH₂)₂CH₃, where z is from 1 to 10, —O(CH₂CH₂O)ᵥCH₃ where v is 0 to 12, in particular 1 or 3, in particular 1, —CH₂CH(CH₃)OCH₃ or —CH₂CH(OH)CH₂OH, or, in a wider sense, another substituent having similar properties, for example, Cl, Br, CF₃, ONO₂, NO₂, NH₂ and O—, S— or NH—C₁–C₄alkyl where Q is, in particular, OH, F, methoxy, preferably 2'-(2-methoxy)ethoxy, or, in particular, H.

Nucleoside building blocks which, in place of the phosphodiester radical, comprise a phosphorothioate radical or a radical which is selected from the following group: phosphodithioate, sulfate, sulfonate, sulfonamide, sulfone, sulfite, sulfoxide, sulfide, formacetal, 3'-thioformacetal, 5'-thioether, hydroxylamine (with CH₂—NH—O—CH₂ in place of the phosphodiester bond O—[(HO—)P(=O)]—O—CH₂), methylene (methylimino) (with CH₂—N(CH₃)—O—CH₃ in place of the phosphodiester bond); methyleneoxy (methylimino) (with CH₂—O—N(CH₃)—CH₂ in place of the phosphodiester bond), methylene ((methylimino)methylimino) (with CH₂—N(CH₃)—N(CH₃)—CH₂ in place of the phosphodiester bond), carbonate, 5'-N-carbamate, amides (with CH₂—(C=O)—NH—CH₂ in place of the phosphodiester bond, cf. International Application WO 92/20823), morpholinocarbamate (cf. Summerton, J. E. and Weller, D. D., U.S. Pat. No. 5,034,506) or peptide nucleic acid (cf. P. E. Nielsen, M. Egholm, R. H. Berg, O. Buchardt, Science 254, 1497 (1991)), all of which belong to the state of the art (for review with references to further information, cf. Milligan et al., J. Med. Chem. 36(14), 1923–37 (1993), and Uhlmann et al., Chemical Reviews 90(4), 543–84 (1990)).

Such 2'-substituted nucleoside building blocks, and such nucleoside building blocks containing the said internucleo sidic bridging groups, and their preparation, are known to the skilled person, as mentioned above, and belong to preferred embodiments of oligonucleotide derivatives according to the invention which, in addition to at least one nucleoside building block of the formula I, possess at least one of the following nucleoside building blocks of the formulae VII to XV or VII* to XV*:

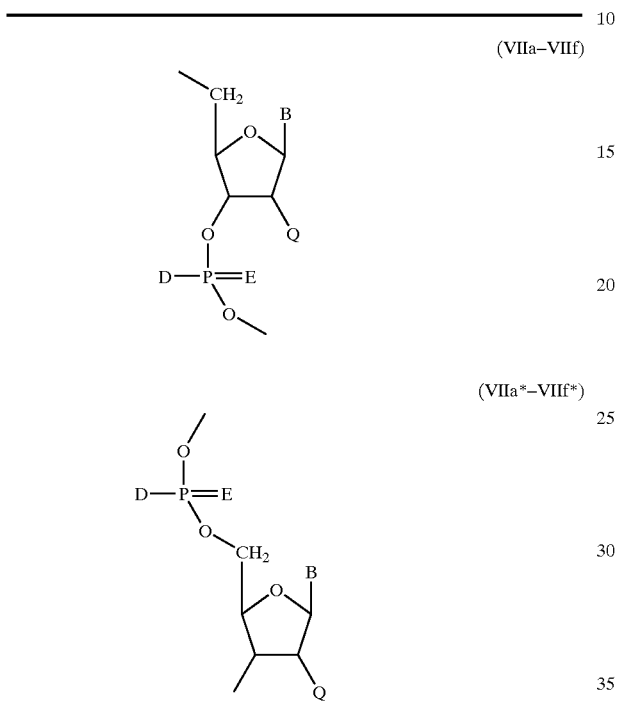

| Radical of the formula | Type | | |
|---|---|---|---|
| (VIIa), (VIIa*) | phosphorothioate | D = SH | E = O |
| (VIIb), (VIIb*) | phosphodithioate | D = SH | E = S |
| (VIIc), (VIIc*) | alkylphosphonate | D = R' | E = O |
| (VIId), (VIId*) | phosphoamidate | D = R'' | E = O |
| (VIIe), (VIIe*) | boranophosphate | D = BH$_3$ | E = O |
| (VIIf), (VIIf*) | phosphotriester | D = O—R''' | E = O | in which R$^I$ is —CH$_3$ or —CH$_2$—CH$_2$—NH$_2$; R$^{II}$ is —N(H)(C$_1$–C$_4$alkyl), —N(H)((CH$_2$)$_3$—N(CH$_3$)$_2$), —N(CH$_3$)(CH$_2$—CH$_2$—N(CH$_3$)$_2$), —N(H)((CH$_2$)$_5$—NH$_2$), —N(H)(CH$_2$—CH$_2$—R$^{IV}$) in which R$^{IV}$=

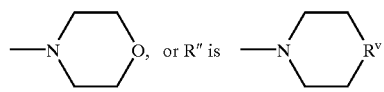, or R'' is in which R$^V$=CH$_2$, O or N(CH$_3$); and R$^{III}$ is C$_1$–C$_4$alkyl;

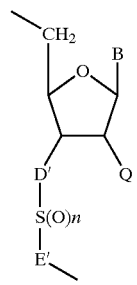

(VIIIa–VIIIe)

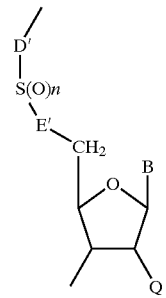

(VIIIa*–VIIIe*)

| Radical of the formula | Type | n | D' | E' |
|---|---|---|---|---|
| (VIIIa), (VIIIa*) | sulfonate | 2 | O | CH$_2$ |
| (VIIIb), (VIIIb*) | sulfone | 2 | CH$_2$ | CH$_2$ |
| (VIIIc), (VIIIc*) | sulfite | 1 | O | O |
| (VIIId), (VIIId*) | sulfoxide | 1 | CH$_2$ | CH$_2$ |
| (VIIIe), (VIIIe*) | sulfide | 0 | CH$_2$ | CH$_2$; |

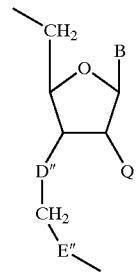

(IXa–IXd)

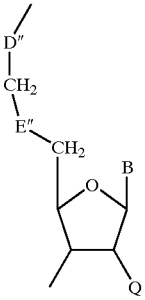

(IXa*–IXd*)

| Radical of the formula | Type | D'' | E'' |
|---|---|---|---|
| (IXa), (IXa*) | formacetal | O | O |
| (IXb), (IXb*) | 3'-thioformacetal | S | O |
| (IXc), (IXc*) | 5'-thioformacetal | O | S |

-continued

| | | | | |
|---|---|---|---|---|
| (IXd), (IXd*) | thioether | CH$_2$ | S | |

(Xa–Xc)

[Structure showing furanose ring with CH$_2$ at 5' position, B base, Q at 3', and CH$_2$-D*-E* substituent]

(Xa*–Xc*)

[Structure showing CH$_2$-D*-E*-CH$_2$ connected to furanose ring with B base and Q]

| Radical of the formula | Type | D* | E* |
|---|---|---|---|
| (Xa), (Xa*) | hydroxylamine | N—H | O |
| (Xb), (Xb*) | methylene(methylimino) | N—CH$_3$ | O |
| (Xc), (Xc*) | methylenoxy(methylimino) | O | N—CH$_3$ |

(XIa–XId)

[Structure showing furanose ring with CH$_2$, B, Q, and D-C(=O)-E substituent]

(XIa*–XId*)

[Structure showing D-C(=O)-E-CH$_2$ connected to furanose ring with B and Q]

| Radical of the formula | Type | D** | E** |
|---|---|---|---|
| (XIa), (XIa*) | carbonate | O | O |
| (XIb), (XIb*) | 5'-N-carbamate | O | NH |
| (XIc), (XIc*) | amide | CH$_2$ | N(R$^{VI}$) |
| (XId), (XId*) | amide II | NH | CH$_2$ | in which R$^{VI}$ is H, methyl or phenyl, preferably H;

(XII)

[Structure showing furanose ring with B, Q, and D$_1$-C(=O)-E$_1$ substituent at 3' position]

(XII*)

[Structure showing D$_1$-C(=O)-E$_1$ connected to furanose ring with B and Q]

| Radical of the formula | Type | D$_1$ | E$_1$ |
|---|---|---|---|
| (XII), (XII*) | amide III | NH | CH$_2$ |

(XIII)

[Structure showing furanose ring with B, Q, and C(=O)-D$_2$-CH$_2$ substituent]

(XIII*)

[Structure showing C(=O)-D$_2$-CH$_2$ connected to furanose ring with B and Q]

| Radical of the formula | Type | D$_2$ |
|---|---|---|
| (XIII), (XIII*) | amide IV | NH |

(XIV)

[Morpholine-type structure with H$_2$C, O, B, N, and O=C-O-CH$_3$ group]

-continued

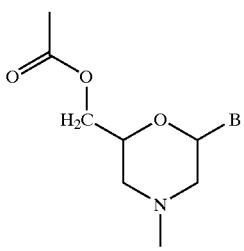

| Radical of the formula | Type |
|---|---|
| IX, IX* | morpholinocarbamate |

(XIV*)

(XV)

(XV*)

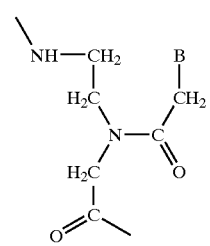

| Radical of the formula | Type |
|---|---|
| XV, XV* | peptide nucleic acid | where Q and B are defined as above, including the given preferences.

In place of at least one phosphodiester bond, a preferred oligonucleotide derivative according to the invention comprises at least one derivatized internucleosidic bridging group, more advantageously one of the abovementioned groups, in particular a phosphorothioate group or an amide group.

In compounds whose terminal nucleoside building block is selected from the formulae VI, VIIa to VIIf, VIIIc, IXa to Ixd, Xa to Xc, XIa to XIc, XIV and XV*, a terminal OH group is preferably bonded to the 5' terminus and a terminal H is bonded to the 3' terminus.

In compounds whose terminal nucleoside building block is selected from the formulae VI*, VIIa*–VIIh*, VIIIa*–VIIIe*, IXa*–IXc*, Xa*–Xc*, XIa*–XId, XII*, XIII* and XV, a terminal H is preferably bonded to the 5' terminus and a terminal OH group is preferably bonded to the 3' terminus.

In compounds which possess a terminal nucleoside building block of the formula XIe, an H is preferably in each case bonded both to the 5' terminus and the 3' terminus.

In compounds which possess a terminal radical of the formulal XIV*, a terminal OH group, which replaces the terminal group —(C=O)—O, is preferably bonded to the 5' terminus and a terminal H is bonded to the 3' terminus.

In compounds whose terminal nucleoside building block is selected from the formulae VIIIb, VIIIb, VIIIb*, VIId, VIIId*, VIIIe, VIIe*, IXd*, XId, XII, XIII and XIII*, a terminal OH group is preferably bonded to the 5' terminus and a terminal OH group is preferably bonded to the 3' terminus.

In an oligonucleotide derivative according to the invention which comprises one or more nucleoside building block(s) of the formula I, the combination with one or more nucleoside building blocks, which can be identical or different, of the formulae VI to XV or VI* to XV* is effected, for example, by one or more building block(s) of the formula I being combined randomly with identical or different nucleoside building block(s) of the formulae VI, XV or VI* to XV*, preferably of the formulae VI, VI*, VIIa, VIIa*, XIc and XIc*. An oligonucleotide derivative according to the invention is further preferred which comprises nucleoside building blocks of the formula I in alternation with identical or different nucleoside building blocks of the formulae VI to XV, in particular of the formulae VI, VI*, VIIa, VIIa*, XIc and XIc*.

An oligonucleotide derivative according to the invention is furthermore preferred in which at least one nucleic acid building block corresponds to the formula I and the remaining nucleic acid building blocks are identical and correspond to a nucleic acid building block of the formulae VI to XV or VI* to XV*, preferably of the formulae VI, VI*, VIIa, VIIa*, XIc and XIc*.

A preferred oligonucleotide derivative according to the invention, which consists exclusively of nucleic acid building blocks of the formula (I), comprises preferably from 3 to 50, more preferably from 10 to 25, in particular 15 to 20, nucleic acid building blocks of the formula (I).

An oligonucleotide derivative according to the invention, which consists both of one or more nucleic acid building block(s) of the formula I and one or more nucleic acid building block(s) of the formulae VI to XV or VI* to XV*, comprises a total of from 3 to 50, preferably from 10 to 25, in particular from 15 to 20, nucleic acid building blocks, of which preferably from 3 to 20, preferably from 5 to 15, are nucleic acid building blocks of the formula (I), which building blocks are distributed randomly in the sequence of the oligonucleotidaderivative, are present in the sequence in alternation with the raising nucleic acid building blocks, or are joined together in the sequence, in particular joined together.

Preferably, an oligonucleotide derivative according to the invention possesses only phosphodiester bonds or only phosphorothioate bonds as the internucleosidic bridging groups.

Preference is furthermore given to oligonucleotide derivatives according to the invention which have a "chimeric" structure. Within the context of the present invention, a "chimeric structure", also termed a "chimera", is to be understood as meaning an oligonucleotide derivative which contains 2 or more chemically different regions which are in each case synthesized from one type of nucleic acid building block. Such chimeric oligonucleotide derivatives typically comprise at least one region of modified nucleic acid building blocks which confer one or more advantageous property/properties (for example increased resistance to nucleases, increased binding affinity or diminished occurrence of sequence-independent side-effects) on the oligonucleotide derivative, the so-called "wing", also designated the M region in that which follows, and a region which enables RNAse H-mediated cleavage of the target nucleic acid to take place, i.e. the so-called "RNAse H window", also designated the U region in that which follows. The affinity of an oligonucleotide or an oligonucleotide derivative is customarily determined by measuring the $T_m$ value of the oligonucleotide (derivative)/target nucleic acid hybrid. The $T_m$ value is the temperature at which the oligonucleotide, or its derivative, and the target nucleic acid dissociate from a previously formed hybrid. The dissociation is determined spectrophotometrically. The higher ther $T_m$ value, the higher is the affinity of the oligonucleotide, or the derivative, for the target nucleic acid. Methods for determining the $T_m$ value belong to the state of the art (cf. Sambrook, Fritsch and Maniatis, "Molecular Cloning—A Laboratory Manual", 2nd Edition, Cold Spring Harbor Laboratory Press, 1989). Within the context of the present invention, increased resistance to nucleases denotes decreased or slowed-down degradation of the oligonucleotide derivatives according to the invention by exonucleases or endonucleases which are present in a cell. The resistance to nucleases or the degradation of an oligonucleotide or a derivative can be monitored by gel electrophoresis, for example. RNAse H is a cellular endonuclease which cleaves the RNA strand of an RNA:DNA duplex. Activation of the enzyme therefore leads to cleavage of the target RNA and consequently increases the efficacy of the antisense mechanism. Cleavage of the target RNA can customarily be demonstrated by gel electrophoresis. Since, in a chimera, different advantageous properties are present in one and the same molecule, oligonucleotide derivatives according to the invention possess a pronounced antisense effect with regard to inhibiting the expression of a protein or RNA.

In one embodiment, a chimeric oligonucleotide derivative according to the invention comprises at least one M region, which consists of at least one nucleic acid building block of the formula I, and at least one U region, which enables RNAse H-mediated cleavage of the target nucleic acid to take place. The U region consists, in particular, of customary 2'-deoxyribonucleic acid building blocks which are linked to each other by way of phosphodiester bonds, or preferably phosphorothioate bonds, as the internucleosidic group. The M region of a chimeric oligonucleotide derivative according to the invention consists, in particular, of nucleic acid building blocks of the formula I in which W and V, as the radical of an internucleosidic bridging group, are a phosphodiester bond, a phosphorothioate bond or an amide bond, with a phosphodiester bond being preferred.

Chimeric oligonucleotide derivatives according to the invention of the abovementioned type, which preferably consist of a total of from 3 to 50, in particular of from 10 to 25, particularly preferably of from 15 to 20, nucleoside building blocks, comprise one or more M region(s) having, for example, from 3 to 25, preferably having from 5 to 15, nucleoside building blocks of the formula I, in which V and W are, in particular, in each case, phosphodiester, phosphorothioate or amide, preferably phosphodiester or phosphorothioate, in particular phosphodiester, as the radical of an internucleosidic bridging group; and one or more U region(s) having, for example, from 3 to 25 2'-deoxyribose building blocks which are not further substituted and which in each case possess a phosphodiester group or phosphorothioate group, preferably a phosphorothioate group, as the radical of an internucleosidic bridging group.

The M and U regions in chimeric oligonucleotide derivatives according to the invention are preferably present in one of the following arrangements:

5'-M-U-M-3'
5'-M-U-3' or
5'-U-M-3'.

Additional oligonucleotide derivatives according to the invention are conjugated with other units, for example a micelle-forming group, an antibody, a carbohydrate, a receptor-binding group, a steroid such as cholesterol, a polypeptide, an intercalating agent, such as an acridine derivative, a long-chain alcohol, a dendrimer, a phospholipid and other lipophilic groups. Conjugating in this way confers advantageous properties with regard to the pharmacokinetic characteristics on the oligonucleotide derivative according to the invention. In particular, conjugating in this way achieves increased cellular uptake.

In a very particularly preferred embodiment, an oligonucleotide derivative according to the invention consists exclusively of nucleoside building blocks of the formula I which are connected to each other by way of phosphodiester bonds as the internucleosidic bridging groups. In another very particularly preferred embodiment, an oligonucleotide derivative according to the invention exclusively comprises nucleoside building blocks of the formula I which are connected to each other by way of phosphorothioate bonds as the internucleosidic bridging groups.

Provided that salt-forming groups are present, the term "oligonucleotide derivative" also encompasses salts, in particular acid addition salts, salts with bases or, if several salt-forming groups are present, possibly also mixed salts or internal salt.

Salts of oligonucleotide derivatives according to the invention are, in particular, pharmaceutically tolerated salts, i.e. essentially nontoxic salts.

Such salts are formed, for example, from the oligonucleotide derivatives according to the invention which possess an acidic group, for example a carboxyl group, a phosphodiester group or a phosphorothioate group, and are, for example, salts with suitable bases. These salts include, for example, nontoxic metal salts which are derived from metals of groups Ia, Ib, IIa and IIb of the Periodic System of the elements, in particular suitable alkali metal salts, for example lithium, sodium or potassium salts, or alkaline earth metal salts, for example magnesium or calcium salts. They furthermore include zinc and ammonium salts and also salts which are formed with suitable organic amines, such as unsubstituted or hydroxyl-substituted mono-, di- or tri-alkylamines, in particular mono-, di- or tri-alkylamines, or with quaternary ammonium compounds, for example with N-methyl-N-ethylamine, diethylamine, triethylamine, mono-, bis- or tris-(2-hydroxy-lower alkyl)amines, such as mono-, bis- or tris-(2-hydroxyethyl)amine, 2-hydroxy-tert-butylamine or tris(hydroxymethyl)methylamine, N,N-di-lower alkyl-N-(hydroxy-lower alkyl)amines, such as N,N-dimethyl-N-(2-hydroxyethyl)amine or tri-(2-hydroxyethyl) amine, or N-methyl-D-glucamine, or quaternary ammonium compounds such as tetrabutylammonium salts.

Lithium salts, sodium salts, magnesium salts, zinc salts or potassium salts are preferred, with sodium salts being particularly preferred.

Oligonucleotide derivatives according to the invention which possess a basic group, for example an amino group or imino group, can form acid addition salts, for example with inorganic acids, for example with a hydrohalic acid, such as hydrochloric acid, sulfuric acid or phosphoric acid, or with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotonic acid or isonicotonic acid, and, in addition, with amino acids, for example with a-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid.

Oligonucleotide derivatives according to the invention which possess both acidic and basic groups can also form internal salts.

Oligonucleotide conjugates according to the invention which possess more than one group which is suitable for salt formation can also form mixed salts.

Pharmaceutically unsuitable salts, for example picrates or perchlorates, can also be used for isolation and purification.

It is only the pharmaceutically tolerated salts, which are nontoxic when used correctly, which are employed for therapeutic purposes and which are therefore preferred.

The invention furthermore provides a compound of the formula (Ia)

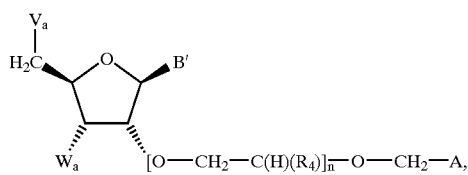

(Ia)

in which

A is a radical of the formula —C(H)($R_3$)—N($R_1$)($R_2$), in which $R_1$ and $R_2$ are, independently of each other, H,
$C_1$–$C_{10}$alkyl,
a radical of the formula II

—(CH$_2$—CH$_2$—X)$_m$—R$_5$    (II), in which each X is, in each case, independently of each other, O or N($R_6$), $R_5$ and $R_6$ are, in each case, independently of each other, H, $C_1$–$C_{10}$alkyl, amino-$C_2$–$C_{10}$alkyl, N-mono-$C_1$–$C_{10}$alkylamino-$C_2$–$C_{10}$alkyl or N,N-di-$C_{10}$alkylamino-$C_2$–$C_{10}$alkyl, and m is an integer from 1 up to and including 3, amino-$C_3$–$C_{10}$alkyl, N-mono-$C_1$–$C_{10}$alkylamino-$C_3$–$C_{10}$alkyl, or N,N-di-$C_1$–$C_{10}$alkylamino-$C_3$–$C_{10}$alkyl; or in which —N($R_1$)($R_2$) are together a radical of the formula (III)

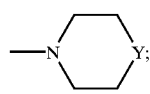

(III)

in which Y is O, S, SO$_2$ or N($R_7$), and $R_7$ is H or —CH$_3$;
$R_3$ is H, —CH$_3$, —CH$_2$CH$_3$, —CH$_2$OH or —CH$_2$—O—$C_1$–$C_4$alkyl; or A is a radical of the formula (IVa) or (IVb)

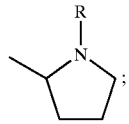

(IVa)

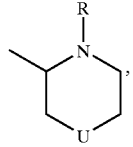

(IVb)

in which R, independently, has the meaning of $R_1$ or $R_2$, and U is O or CH$_2$;
$R_4$ is H, —CH$_3$, —CH$_2$CH$_3$, —CH$_2$OH or —CH$_2$—O—$C_1$–$C_4$alkyl;
n is 0, 1 or 2;
B' is the radical of a protected or unprotected nucleic acid base; and
$V_a$ and $W_a$ are, independently of each other, —OH, —NH$_2$ of identically or differently protected hydroxyl or amino groups,
where those compounds are excepted in which, in the radical A, two heteroatoms are linked to the same carbon atom, and where other reactive groups are present in protected or unprotected form.

In a further embodiment of the radical of formula (III) Y is SO.

A compound of the formula (Ia) is preferred in which
A is a radical of the formula —C(H)($R_3$)—N($R_1$)($R_2$), in which
$R_1$ and $R_2$ are, independently of each other, H, $C_1$–$C_5$alkyl, amino-$C_2$–$C_5$alkyl, N-mono-$C_1$–$C_3$alkylamino-$C_2$–$C_5$alkyl, N,N-di-$C_1$–$C_3$alkylamino-$C_2$–$C_5$alkyl or a radical of the formula II

—(CH$_2$—CH$_2$—X)$_m$—R$_5$    (II), in which X is O or N($R_6$), $R_5$ and $R_6$ are, independently of each other, H, $C_1$–$C_3$alkyl, amino-$C_2$–$C_3$alkyl, N-mono-$C_1$–$C_3$alkylamino-$C_2$–$C_5$alkyl or N,N-di-$C_1$–$C_3$alkylamino-$C_2$–$C_5$alkyl, and m is 1; and where $R_3$ has the said meanings and is, in particular, H.

A compound of the formula (Ia) is further preferred in which
$R_1$ and $R_2$ are, independently of each other, H, methyl, ethyl, aminoethyl, aminopropyl, N-monomethylaminoethyl, N-monomethylaminopropyl, N-monoethylaminoethyl, N-monoethylaminopropyl, N,N-dimethylaminoethyl, N,N-dimethylaminopropyl, N,N-diethylaminoethyl, N,N-diethylaminopropyl, or a radical of the formula II

—(CH$_2$—CH$_2$—X)$_m$—R$_5$    (II), in which X is O or N($R_6$), $R_5$ and $R_6$ are, independently of each other, H, methyl, ethyl or propyl, and m is 1.

A compound of the formula (Ia) is particularly preferred in which $R_1$ and $R_2$ are, independently of each other, H, methyl, ethyl, aminoethyl, N-monomethylaminoethyl, N-monoethylaminoethyl, N,N-dimethylaminoethyl or N,N-diethylaminoethyl.

In particular, $R_1$ and $R_2$ are, independently of each other, H, methyl or ethyl.

In an advantageous embodiment of the compound of the formula (Ia), $R_1$ and $R_2$ are in each case H, or $R_1$ and $R_2$ are in each case methyl, or one of the substituents $R_1$ and $R_2$ is H and the other is methyl.

In this context, in particular, $R_1$ and $R_2$ are in each case methyl, or one of the substituents $R_1$ and $R_2$ is H and the other is methyl.

In the compounds of the formula (Ia) according to the invention, including the said preferences, $R_3$ and $R_4$ are, independently of each other, H, —$CH_3$, —$CH_2OH$ or —$CH_2$—O—$CH_3$.

Preference is given to compounds of the formula (Ia) according to the invention, including the said preferences, in which n is 0.

Compounds of the formula (Ia) according to the invention are particularly advantageous in which n is 0 and A is a radical of the formula —C(H)(R3)—N($R_1$)($R_2$) in which R3 is H and $R_1$ and $R_2$ are defined as above, including the said preferences.

A compound of the formula (Ia) according to the invention is furthermore preferred in which A is a radical of the formula —C(H)($R_3$)—N($R_1$)($R_2$), in which —N($R_1$)($R_2$) is a radical of the said formula (III), where particular preference is given to Y being N($R_7$) and $R_7$ being H or, particularly preferably —$CH_3$; in this context, n is preferably 0, $R_3$ is preferably H.

An embodiment which is further preferred relates to a compound of the formula (Ia) according to the invention in which A is a radical of the abovementioned formula (IVa), where R is particularly preferably H or $C_1$–$C_{10}$alkyl, in particular H; in this context, n is preferably 0.

In the compounds of the formula (Ia), other reactive groups in the 2' substituent, for example an unsubstituted or monosubstituted amino group in the said substituent A, can be present in protected form, with the compounds of the formula (Ia) which are present in protected form being particularly suitable for oligonucleotide synthesis.

The invention furthermore relates to compounds of the formula (Ia) according to the invention, including the said preferences, in which B' is a radical of the formula (V1) to (V14)

(V1)

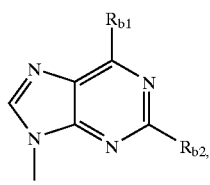

(V2)

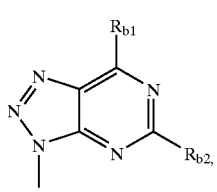

-continued (V3)

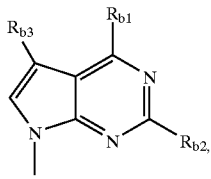

(V4)

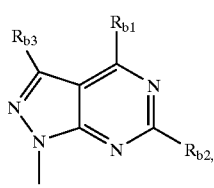

(V5)

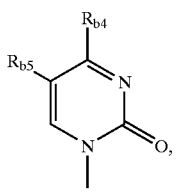

(V6)

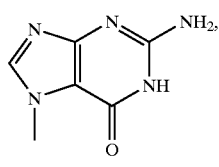

(V7)

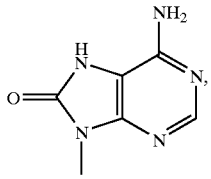

(V8)

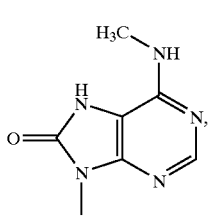

(V9)

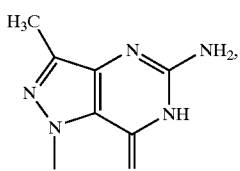

(V10)

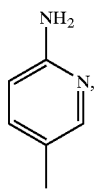

-continued

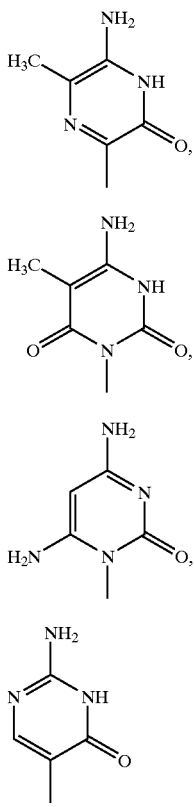

(V11)

(V12)

(V13)

(V14)

in which
R$_{b1}$ is —NH$_2$, —SH or —OH;
R$_{b2}$ is H, —NH$_2$ or —OH; and
R$_{b3}$ is H, Br, I, —CN, —C≡C—CH$_3$, —C(O)NH$_2$ or —CH$_3$;
R$_{b4}$ is —NH$_2$ or —OH; and
R$_{b5}$ is H, F, Br, I, —CN, —C≡C—CH$_3$, —C(O)NH$_2$ or —CH$_3$;

with exocyclic amino groups being present in unprotected or protected form.

A compound of the formula (Ia) is preferred in which

B' is a radical of the formula (V1), (V2), (V3), (V4) or (V5)

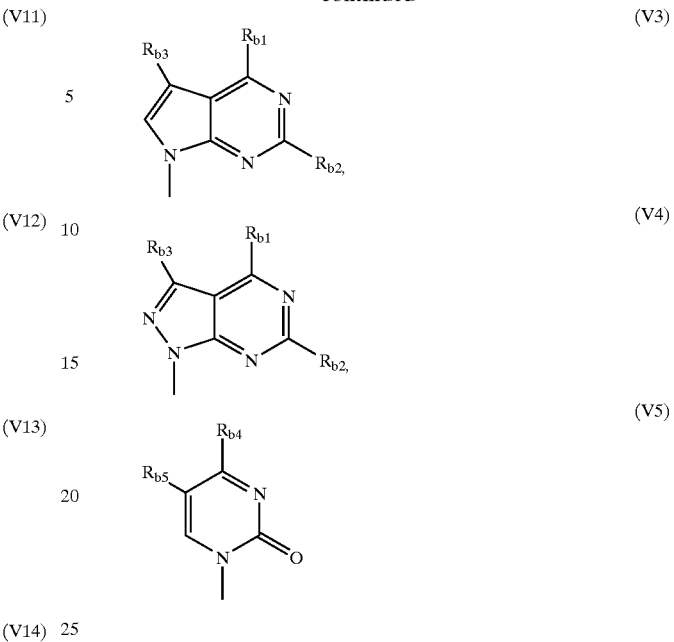

(V1)

(V2)

(V3)

(V4)

(V5)

in which
R$_{b1}$ is —NH$_2$, —SH or —OH;
R$_{b2}$ is H, —NH$_2$ or —OH; and
R$_{b3}$ is H, Br, I, —CN, —C≡C—CH$_3$, —C(O)NH$_2$ or —CH$_3$;
R$_{b4}$ is —NH$_2$ or —OH; and
R$_{b5}$ is H, F, Br, I, —CN, —C≡C—CH$_3$, —C(O)NH$_2$ or —CH$_3$, with exocyclic amino groups being present in unprotected or protected form.

B' in a compound of the formula (Ia) is, in particular, selected from the group of the following radicals: xanthine, hypoxanthine, adenine, 2-aminoadenine, guanine, 6-thioguanine, uracil, thymine, cytosine, 5-methylcytosine, 5-propynyluracil, 5-flourouracil and 5-propynylcytosine, with exocyclic amino groups being present in protected or unprotected form.

Protecting groups for amino groups and hydroxyl groups, in particular in the case of nucleic acid bases or in the case of a sugar residue in a nucleoside, and methods for derivatizing these functional groups, are well known in sugar chemistry and nucleic acid chemistry and are applicable to the present invention (cf., for example, Beaucage, S. L. et al., Tetrahedron 48 (1992), 2223–2311; J. F. W. McOmie, "Protective Groups in Organic Chemistry", Plenum Press, London and New York 1973; Th. W. Greene, "Protective Groups in Organic Synthesis", Wiley, New York 1981, in "The Peptides", Volume 3 (E. Gross and J. Meienhofer, eds.), Academic Press, London und New York 1981; Greene, B. T., "Protective Groups in Organic Synthesis", Wiley Interscience, New York (1991); Sonveaux, E., Bioorganic Chemistry 14, 274–325 (1986); "Methoden der organischen Chemie" (Methods of organic chemistry), Houben-Weyl, 4th Edition, Vol.15/I, Georg Thieme Verlag, Stuttgart 1974; H.-D. Jakubke and H. Jescheit, "Aminosäuren, Peptide, Proteine" (Amino acids, Peptides and Proteins), Verlag Chemie, Weinheim, Deerfield Beach and Basle 1982). Examples of these protecting groups are: benzyl, methylbenzyl, dimethylbenzyl, methoxybenzyl, dimethoxybenzyl, bromobenzyl, 2,4-dichlorobenzyl; diphenylmethyl, di(methylphenyl)methyl, di(dimethylphenyl)methyl, di(methoxyphenyl)methyl, di(dimethoxyphenyl)methyl, triphenylmethyl, tris-4,4', 4"-tert-butylphenylmethyl, di-p-anisylphenylmethyl, tri (methylphenyl) methyl, tri (dimethylphenyl) methyl, methoxyphenyl (diphenyl) methyl, di (methoxyphenyl) phenylmethyl, tri (methoxyphenyl) methyl, tri (dimethoxyphenyl)methyl; triphenylsilyl, alkyldiphenylsilyl, dialkylphenylsilyl and trialkylsilyl having from 1 to 20, preferably from 1 to 12 and particularly preferably from 1 to 8 C atoms in the alkyl groups, for example trimethylsilyl, triethylsilyl, tri-n-propylsilyl, isopropyl-dimethylsilyl, tert-butyldimethylsilyl, tert-butyidiphenylsilyl, n-octyldimethylsilyl, (1,1,2,2-tetramethylethyl)dimethylsilyl; —($C_1$–$C_8$alkyl)$_2$Si—O—Si ($C_1$–$C_8$alkyl)$_2$-, in which alkyl is, for example, methyl, ethyl, n- and iso-propyl or n-, iso- or tert-butyl; $C_2$–$C_{12}$—, in particular $C_2$–$C_8$acyl, for example acetyl, propanoyl, butanoyl, pentanoyl, hexanoyl, benzoyl, methylbenzoyl, methoxybenzoyl, chlorobenzoyl and bromobenzoyl; $R_{S1}$—$SO_2$—, in which $R_{S1}$ is $C_1$–$C_{12}$alkyl, in particular $C_1$–$C_6$alkyl, $C_5$- or $C_6$cycloalkyl, phenyl, benzyl, $C_1$–$C_{12}$- and, in particular, $C_1$–$C_4$alkylphenyl, or $C_1$–$C_{12}$- and, in particular, $C_1$–$C_4$alkylbenzyl, or halophenyl or halobenzyl, for example methyl-, ethyl-, propyl-, butyl-, phenyl-, benzyl-, p-bromo-, p-methoxy- and p-methylphenylsulfonyl; $C_1$–$C_{12}$-, preferably $C_1$–$C_8$alkoxycarbonyl, which is unsubstituted or substituted by F, Cl, Br, $C_1$–$C_4$alkoxy, tri-($C_1$–$C_4$alkyl)silyl or $C_1$–$C_4$alkylsulfonyl, for example methoxy-, ethoxy-, n- or iso-propoxy- or n-, iso- or tert-butoxycarbonyl, 2-trimethylsilylethoxycarbonyl, 2-methylsulfonylethoxycarbonyl, allyloxycarbonyl, or phenyloxycarbonyl which is unsubstituted or substituted as in the case of alkoxycarbonyl, or benzyloxycarbonyl, for example methyl-, methoxy- or chlorophenyloxycarbonyl, or -benzyloxycarbonyl, and also 9-fluorenylmethyloxycarbonyl. Provided tha t a protecting group is alkyl, this radical can be substituted by F, Cl, Br, $C_1$–$C_4$alkoxy, phenyloxy, chlorophenyloxy, methoxyphenyloxy, benzyloxy, methoxybenzyloxy or chlorophenyloxy.

A protected amino group can, for example, beprotected in a form of an acylamino, arylamino, methylamino, etherified mercaptoamino, 2-acyl-lower alk-1-enylamino, silylamino or N-lower alkyl-pyrrolidinylidene group or in the form of ansazido group.

In a corresponding acylamino group, acyl is, for example, the acyl radical of an organic carboxylic acid which possesses, for example, not more than 18 C atoms, in particular an unsubstituted or substituted, for example substituted by halogen or aryl, lower alkane carboxylic acid, or an unsubstituted or substituted, for example halogen-, lower alkoxy- or nitro-substituted benzoic acid, or preferably a carbonic acid semiester. Examples of such acyl groups are lower alkanolyl, such as formyl, acetyl, propionyl, isobutyryl or pivaloyl; halogen-lower alkanoyl, for example 2-haloacetyl, such as 2-chloro-, 2-bromo-, 2-iodo-, 2,2,2-triflouro- or 2,2,2-trichloro-acetyl; phenoxy- or (lower alkoxy)phenoxy-lower alkyl, such as phenoxyacetyl or 4-tert-butylphenoxyacetyl; unsubstituted or substituted, for example halogen-, lower alkoxy- or nitro-substituted, benzoyl, such as benzoyl, 4-chlorobenzoyl, 4-methoxybenzoyl or 4-nitrobenzoyl; lower alkoxycarbonyl, preferably lower alkoxycarbonyl which is branched in the 1 position of the lower alkyl radical or is suitably substituted in the 1 or 2 positions, for example tert-lower alkoxycarbonyl, such as tert-butoxycarbonyl; arylmethoxycarbonyl having one, two or three phenyl radicals which are unsubstituted or monosubstituted or polysubstituted by, for example, lower alkyl, in particular tert-lower alkyl, such as tert-butyl, lower alkoxy, such as methoxy, hydroxyl, halogen, such as chlorine, and/or nitro, for e xample benzyloxycarbonyl, 4-nitrobenzyloxycarbonyl, diphenylmethoxycarbonyl, 9-flororenylmethoxycarbonyl or di(4-methoxyphenyl)-methoxycarbonyl; aroylmethoxycarbonyl, in which the aroyl group is preferably benzoyl which is unsubstituted or substituted, for example by halogen such as bromine, for example phenacyloxycarbonyl; 2-halogen-lower alkoxycarbonyl, for ex ample 2,2,2-trichloroethoxycarbonyl, 2-bromoethoxycarbonyl or 2-iodoethoxycarbonyl; 2-(trisubstituted silyl)-lower alkoxycarbonyl, for example 2-lower alkylsilyl-lower alkoxycarbonyl, such as 2-trimethylsilylethoxycarbonyl or 2-(di-n-butylmethylsilyl) ethoxycarbonyl; triarylsilyl-lower alkoxycarbonyl, for example 2-triphenylsilylethoxycarbonyl; or N,N-di-lower alkylformamidinyl, such as N,N-dimethylformamidinyl.

In an arylmethylamino group, for example a mono-, di- or, in particular, triarylmethylamino group, the aryl radicals are, in particular, unsubstituted or substituted phenyl radicals. Examples of such groups are benzyl-, diphenylmethyl- or, in particular, tritylamino.

In an etherified mercaptoamino group, the mercapto group is present, in particular, in the form of a substituted arylthio- or aryl-lower alkylthio group, in which aryl is, for example, phenyl which is unsubstituted or, for example, substituted by lower alkyl, such as methyl or tert-butyl, lower alkoxy, such as methoxy, halogen, such as chlorine, and/or nitro, for example 4-nitrophenylthio.

In a 2-acyl lower alk-1-enyl radical, which can be used as an amino protecting group, acyl is, for example, the corresponding radical of a lower alkanecarboxylic acid; of a benzoic acid which can be unsubstituted or, for example, substituted by lower alkyl, such as methyl or tert-butyl, lower alkoxy, such as methoxy, halogen, such as chlorine, and/or nitro; or, in particular, a carbonic acid semiester, such as a carbonic acid lower alkyl semiester. Corresponding protecting groups are, in particular, 1-lower alkanoyl-lower alk-1-en-2-yl, for example 1-lower alkanoylprop-1-en-2yl, for example 1-acetylprop-1-en-2-yl, or lower alkoxycarbonyl-lower alk-1-en-2-yl, for example lower alkoxycarbonylprop-1-en-2-yl, such as 1-ethoxycarbonylprop-1-en-2-yl.

A silylamino group is, for example, a tri-lower alkylsilylamino group, for example trimethylsilylamino or tert-butyldimethylsilylamino. The silicon atom of the silylamino group can also be substituted by only two lower alkyl groups, for example methyl groups. Compounds which possess such protecting groups can be prepared, for example, using the corresponding chlorosilanes, such as dimethylchlorosilane, as silylating agents.

An N-lower alkylpyrrolidinylidene group is, preferably, N-methylpyrrolidin-2-ylidene.

Preferred amino protecting groups are lower alkoxycarbonyl, phenyl-lower alkoxycarbonyl, fluorenyl-lower alkoxycarbonyl, 2-lower alkanoyl-lower alk-1-en-2-yl and lower alkoxycarbonyl-lower alk-1-en-2-yl, particularly preferably isobutyryl, benzoyl, phenoxyacetyl, 4-tert-butylphenoxyacetyl, N,N-dimethylformamidinyl and N-methylpyrrolidin-2-ylidene.

When $V_a$ and $W_a$ are protected hydroxyl or amino groups, the protecting groups can be different or, preferably, identical. Protecting groups on a nucleic acid base B' can be different or, preferably, identical.

In a particularly preferred embodiment, protecting groups for $V_a$ ad $W_a$, as protected hydroxyl or amino groups, are selected from the following group: benzyl, methylbenzyl, dimethylbenzyl, methoxybenzyl, dimethoxybenzyl, halogenated benzyl, in particular bromobenzyl; diphenylmethyl, di(methylphenyl) methyl, di(dimethylphenyl) methyl, di(methoxyphenyl)methyl, di(methoxyphenyl) (phenyl) methyl, triphenylmethyl, tris-4,4', 4"-tert-butylphenylmethyl, di-p-anisylphenylmethyl, tri(methylphenyl)methyl, tri(dimethylphenyl) methyl, tri(methoxyphenyl)methyl, tri(dimethoxyphenyl)methyl; trimethylsilyl, triethylsilyl, tri-n-propylsilyl, i-propyldimethylsilyl, t-butyldimethylsilyl, t-butyldiphenylsilyl, n-octyldimethylsilyl, (1,1,2,2-tetramethylethyl)dimethylsilyl, —($CH_3$)$_2$Si-O-Si($CH_3$)$_2$—, —(i-$C_3H_7$)$_2$Si—O—Si(i-$C_3H_7$)$_2$-; acetyl, propanoyl, butanoyl, pentanoyl, hexanoyl, benzoyl, methylbenzoyl, methoxybenzoyl, chlorobenzoyl and bromobenzoyl; methyl-, ethyl-, propyl-, butyl-, phenyl-, benzyl-, p-bromo-, p-methoxy- and p-methylphenylsulfonyl; methoxy-, ethoxy-, n- or i-propoxy- or n-, i- or t-butoxycarbonyl, or phenyloxycarbonyl, benzyloxycarbonyl, methyl- or methoxy- or chlorophenyloxycarbonyl or -benzyloxycarbonyl or 9-fluorenylmethyloxycarbonyl.

Within the context of the present invention, the prefix "lower" denotes a radical of from 1 up to and including 7, preferably of from 1 up to and including 4, particularly preferably of from 1 up to and including 2, C atoms, unless otherwise indicated.

A compound of the formula (Ia) including the said preferences, is preferred in which the protecting group for exocyclic amino groups of the nucleic acid base B' is selected from the following group: —C(O)$CH_3$, —C(O)—CH($CH_3$)$_2$, —C(O)-phenyl, —C(O)—$CH_2$—C-phenyl, —C(O)—CH-p-(tert-butyl)phenyl, —C(O)—$CH_2$—O—p-(tert-butyl)phenyl, —C(O)—$CH_2$—O-p-(isopropyl)phenyl, =CH—N($CH_3$)$_2$, =CH—N(butyl)$_2$ and

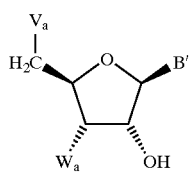

A compound of the formula (Ia), including the said preferences, is furthermore preferred in which the protecting group for $V_a$ or $W_a$, as a protected hydroxyl group or as a protected amino group, is a trityl-type protecting group. This trityl-type protecting group is preferably selected from the following group: trityl, 4-monomethoxytrityl, 4,4'-dimethoxytrityl and 4,4', 4"-tris-tert-butyltrityl.

The compounds of the formula (Ia) can be prepared in a manner known per se.

The invention also provides a process for preparing a compound of the formula (Ia),

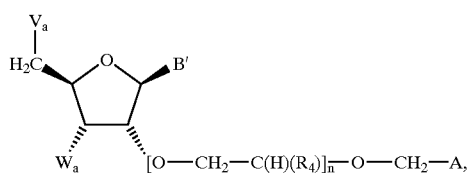 (Ia)

in which $V_a$, $W_a$, A and B' are defined as above, including the said preferences, and
   (a) $R_4$ is H, —$CH_3$, —$CH_2CH_3$, —$CH_2OH$ or —$CH_2$—O—$C_1$-$C_4$alkyl, and n is 0, which comprises reacting a compound of the formula (A)

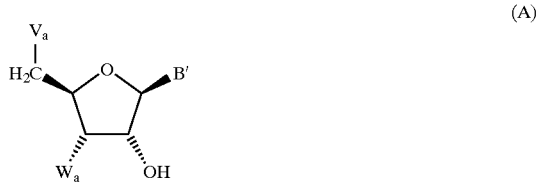 (A)

in which $V_a$ and $W_a$ are, independently of each other, a protected hydroxyl or amino group, and B' is defined as above, with exocyclic amino groups in B' being protected by protecting groups,
with a compound of the formula (B)

X—$CH_2$—A     (B), in which X is Cl, Br, I, tosyl-O or mesyl-O, and A is defined as above, with primary and secondary amino groups and primary hydroxyl groups in A being protected by protecting groups; or
   (b) $R_4$ is H, —$CH_3$, —$CH_2CH_3$, —$CH_2OH$ or —$CH_2$—O—$C_1$-$C_4$alkyl and n is 1 or 2,
which comprises reacting a comDound of the formula (A)

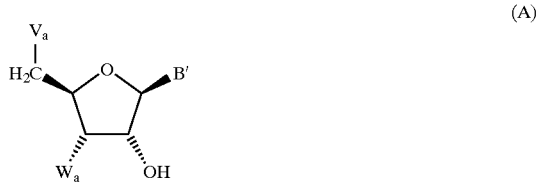 (A)

in which $V_a$, and $W_a$, are, independently of each other, a protected hydroxyl or amino group, and B is defined as above, with exocyclic amino groups in B' being protected by the protecting groups,
with a compound of the formula (C)

X—$CH_2$—C(H) ($R_4$)—[O—$CH_2$—C(H) ($R_4$)]$_{(n-1)}$—O—$CH_2$—A     (C)

in which X is Cl, Br, I, tosyl-O or mesyl-O, and $R_4$ and A are defined as above, with primary and secondary amino groups and primary hydroxyl groups in A being protected by protecting groups; or
   (c) $R_4$ is H and n is 1 or 2,
which comprises reacting a compound of the formula (D)

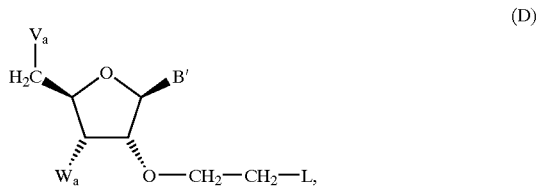 (D)

in which $V_a$ and $W_a$ are, independently of each other, a protected hydroxyl or amino group, B' is defined as above, with exocyclic amino groups in B' being protected by protecting groups, and L is a leaving group,
with a compound of the formula (E)

HO—($CH_2$—$CH_2$)$_{n-1}$—O—$CH_2$—A     (E)

in which A is defined as above, and with primary and secondary amino groups and primary hydroxyl groups in A being protected by protecting groups; or (d) $R_4$ is H, n is 0, and A is a radical of the formula
—C(H)($R_3$)—N($R_1$)($R_2$), which comprises reacting a compound of the formula (D)

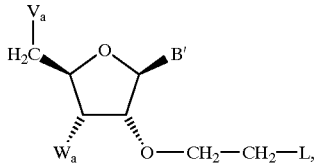
(D)

which is defined as above,
with a compound of the formula (F)

NH($R_1$)($R_2$) 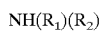 (F)

in which $R_1$, $R_2$ or the group —N($R_1$)($R_2$) are defined as above, and with functional groups in $R_1$ or $R_2$ being protected if necessary; or (e) $R_4$ is H, n is 0 and A is a radical of the formula
—C(H)($R_3$)—N($R_1$)($R_2$), which comprises reacting a compound of the formula (D)

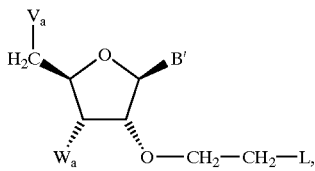
(D)

which is defined as above,
with an azide and subsequent reduction, if necessary using a catalyst, for example $SnCl_2$, to give a compound of the formula (G)

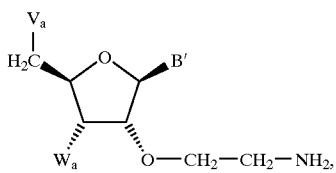
(G)

and, if necessary, subjecting the compound of the formula (G) to further derivatization;
with, in cases (a) to (e), protected groups subsequently being deprotected if necessary.

The compounds of the formulae (A), (B), (C), (E) and (F) are known and are commercially available or can be prepared using methods which are known per se.

A compound of the formula (D) can be prepared, for example, by reacting a compound of the formula (A), which is defined as above, with a compound of the formula (H)

X—CH$_2$—C(O)O$R_{10}$ 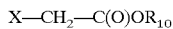 (H), in which $R_{10}$ is $C_1$–$C_4$alkyl and X is Cl, Br, I, tosyl-O or mesyl-O, in a solvent, reducing the ester function of the resulting compound, preferably with $NaBH_4$, to give a primary alcohol of the formula (K)

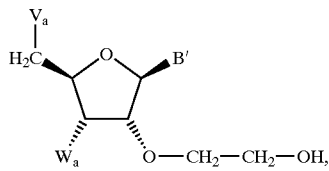
(K)

in which $V_a$, $W_a$ and B' are defined as above, and converting the primary alcohol group of the compound of the formula (K), in a manner known per se, into a leaving group L, preferably tosyl-O or mesyl-O, thereby obtaining a compound of the formula (D)

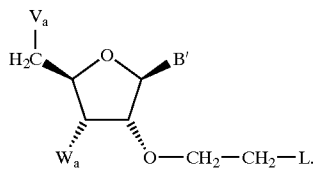
(D).

Reactions of the type described, and suitable reaction conditions, are known to the skilled person (cf., for example, Martin, P., Helv. Chem. Acta, 78 (1995), 486 ff.; Lesnik, E. A. et al., Biochemistry, 32 (1993), 7832 ff.; Inoue, H. et al., Nucl. Acids Res. 15 (1987) 6131 ff.; Manoharan, M. et al., Tetrahedron Lett. 32 (1991), 7171 ff.; Keller, T. H. et al., Helv. Chimia Acta 76 (1993), 884ff; Sproat, B. S. et al., Nucl. Acids Res. 17 (1989), 3373ff.; International Applications WO 94/02501; WO 95/16696; WO 91/06556; WO 93/07883; WO 91/15499; DE 91-4110085; WO 95/06659; the entire content of these publications is hereby incorporated by reference).

In the reactions described, the reaction temperature is between –50° C. and 200° C., preferably between –10° C. and 90° C.

The compounds of the formula (Ia) are isolated and purified using methods which are known per se, for example precipitation, crystallization, filtration and chromatographic methods.

A compound of the formula (Ia) is suitable, in particular, as a synthesis building block or intermediate for preparing an oligonucleotide derivative according to the invention.

Accordingly, the invention also provides a process for preparing an oligonucleotide according to the invention, which process comprises the following steps:
(i) converting a compound of the formula (Ia) into a form which is suitable for oligonucleotide synthesis,
(ii) using the compound of the formula (Ia), which is present in a suitable form, in oligonucleotide synthesis.

The invention also provides the use of a compound of the formula (Ia) according to the invention as a nucleoside building block in oligonucleotide synthesis, if desired after converting it into a form which is suitable for oligonucleotide synthesis.

Within the context of the present invention, the expression "conversion into a form which is suitable for oligonucleotide synthesis" denotes, in particular, that the 5' and/or 3' hydroxyl group of a protected or unprotected compound of the formula (Ia) is/are converted into (a) radical(s) which is/are capable, in association with the subsequent oligonucleotide synthesis, of forming (an) internucleosidic bridging group(s), in particular (a) bridging group(s) of the abovementioned type. Methods for converting the 3' or 5' hydroxyl group(s) into such radicals are known (cf., for example, the abovementioned publications by De Mesmaeker, A., and Crooke, S. T.; the entire content of these publications is hereby incorporated by reference).

The compounds of the formula (Ia), which can be present in suitable form, are employed as nucleoside building blocks in the synthesis of the oligonucleotide derivatives according to the invention. The oligonucleotides according to the invention can be prepared, in a manner known per se, in accordance with a variety of methods, in DNA synthesis equipment which can be automated and which can be obtained commercially in conjunction with method protocols. For example, in the case of a phosphodiester group as the internucleosidic bridging group, the phosphotriester method, the phosphite triester method or the H-phosphonate method, which are familiar to the skilled person, can be used (cf., for example, Eckstein, F., "Oligonucleotides and Analogues, A Practical Approach", IRL Press (1991); the entire content of this publication is hereby incorporated by reference).

In the case of the phosphite triester method, the approach can, for example, be to react, for example, a nucleoside building block of the formula (Ia), in which $V_a$ and $W_a$ are in each case —OH, with a protecting group reagent, for example 4,4'-dimethoxytriphenylmethyl chloride, to give a nucleoside of the formula (Ib)

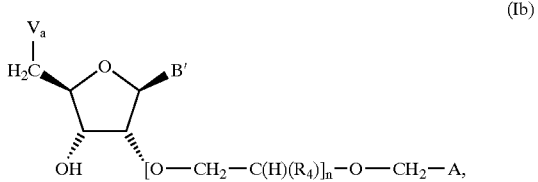

in which $V_a$ is a protected hydroxyl group and A, B' and $R_4$ are defined as above for the compound of the formula (Ia) including the said preferences, and to bind the compound of the formula Ib with the aid of a linker, for example succinic anhydride, to a solid support material, for example to "Controlled Pore Glass" (CPG), which contains long-chain alkylamino groups. In a separate procedure, the hydroxyl group of another nucleoside building block of the formula (Ib) is derivatized, for example using $R^xO$—$P[N(i\text{-propyl})_2]_2$ to give a phosphoramidite of the formula (Ic)

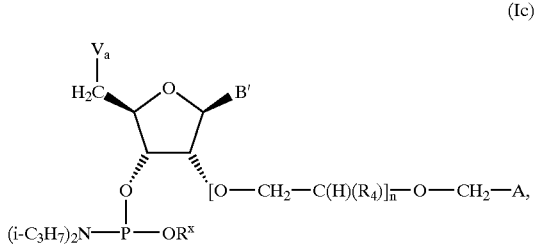

in which $R^x$ is a customary protecting group, for example β-cyanoethyl. Such a compound of the formula. (Ic) is another important intermediate and constitutes another part of the subject-matter of the present invention.

Protecting groups which are mentioned above for the radical $V_a$ as protected hydroxyl group in compounds of the formula (Ia) are also preferred protecting groups for the radical $V_a$ in compounds of the formula (Ib) or (Ic). Thus, in compounds of the formula (Ib) or (Ic), an hydroxyl group which is protected with a trityl-type group is preferred as radical $V_a$, with the trityl-type group being selected, in particular, from trityl (Tr), 4-monomethoxytrityl (MMTr), preferably 4,4'-dimethoxytrityl (DMTr) and, likewise preferably, 4,4', 4''-tris-tert-butyltrityl (TTTr).

After the protecting group on the radical $V_a$, for example the DMTr- or the TTTr group, of the support-bound material has been eliminated, this material is coupled, with elimination of —$N(i\text{-}C_3H_7)_2$ to the compound of the formula (Ic), any free hydroxyl groups which may be present are blocked ("capping") and the phosphite which has been formed is then oxidized, thereby leading, for example, to the phosphate or phosphorothioate. After the dimer has been deprotected, the reaction cycle is repeated with a compound of the formula (Ic) until an oligomer having the desired number of monomer units has been synthesized, and the product is then detached from the support material. In this way, an oligonucleotide derivative according to the invention is obtained which is synthesized entirely from nucleoside building blocks of the formula (Ia) having phosphodiester groups or phosphorothioate groups, depending on the oxidation conditions, as the internucleosidic bridging group. Depending on the use of appropriate nucleoside building blocks in the individual reaction cycles, oligonucleotides according to the invention of any arbitrary sequence can be prepared in an analogous manner, in particular those oligonucleotides according to the invention which, in addition to one or more nucleoside building block(s) of the formula (Ia), contain other nucleoside building blocks, in particular those of the abovementioned type.

Oligonucleotide derivatives according to the invention which do not contain, or which do not exclusively contain, phosphodiester groups or phosphorothioate groups as the internucleosidic bridging groups can be prepared in a manner known per se (cf., for example, the abovementioned publications of De Mesmaeker, A., or Crooke, S. T.).

As mentioned above, the oligonucleotide derivatives according to the invention possess a number of advantageous properties. These include, in particular, a high binding affinity for a target nucleic acid and a high resistance to nucleases. Furthermore, they are capable of a sequence-specific effect, are taken up satisfactorily by a cell and have adequate bioavailability. These properties make the oligonucleotides according to the invention particularly suitable for pharmaceutical applications, in particular for modulating the expression of a protein. Another preferred pharmaceutical application is modulation of the expression of an RNA molecule, in particular at the transcription step.

An oligonucleotide derivative according to the invention can be used, in particular, as an antisense oligonucleotide. The expression "antisense" is known to the skilled person and, in the context of the present invention, characterizes, in particular, the relationship between an oligonucleotide derivative according to the invention and the sequence, which is complementary to it, of a target nucleic acid, namely that the oligonucleotide derivative and the complementary sequence are able to hybridize to each other. The identification of a suitable antisense oligonucleotide is a multi-step process. First of all, a target nucleic acid is identified which underlies the protein whose expression characterizes a pathological state in a mammalian subject, including man, and is to be modulated. A suitable target nucleic acid is, in particular, the RNA which is transcribed from the gene which encodes the protein of interest, such as pre-mRNA or, preferably, the (mature) mRNA. In principle, modulation of expression with the aid of an antisense oligonucleotide can also take place at the chromosomal level. Within the target nucleic acid, a sequence or sequences is/are identified which interact, in particular by means of hybridization, with the oligonucleotide derivative according to the invention such that expression of the protein of interest is modulated. An oligonucleotide derivative according to the invention must possess a complementarity to the target nucleic acid which is adequate, due to sufficiently powerful and sufficiently specific hybridization, to achieve the desired effect.

Consequently, the invention also provides the use of an oligonucleotide derivative according to the invention, including the said preferences, as an antisense oligonucleotide. In this context, oligonucleotide derivatives according to the invention are preferred which have, as the nucleic acid base B, a radical of the formula (V1), (V2), (V3), (V4) or (V5), which are defined above.

Oligonucleotide derivatives according to the invention are also able specifically to recognize a double-stranded DNA sequence and to form, with a high degree of affinity, a triple helix ("triplex") with this DNA sequence. Triplex-forming oligonucleotides, which can also be modified, are able selectively to modulate the transcription of a gene into an RNA, and consequently to modulate the expression of a protein, and are familiar to the skilled person (cf., for example, the above-listed publications by Cohen, J. S. et al.; Stull, R. et al.; or Plum, G. E. et al.).

Consequently, the invention also provides the use of an oligonucleotide derivative according to the invention, including the said preferences, as a triplex-forming oligonucleotide. In this context, the radicals of the formulae (V1) to (V14), in particular the radicals of the formulae (V1 to V5) which are defined as above, are preferred, in particular, as the nucleic acid base B.

Consequently, according to the invention, oligonucleotide derivatives are preferred which are capable of modulating the expression of a protein or of an RNA molecule, for example an mRNA.

Within the context of the present invention, "modulation" of the expression of a protein or an RNA molecule denotes, in particular, a partial or complete inhibition of the expression, or in particular of translation or transcription. Such an inhibition, in particular due to partial or complete degradation of the target nucleic acid, due to the process for translating the target nucleic acid being completely or partially inhibited, or due to the transcription process being completely or partially inhibited, can be determined by means of known methods, for example by means of the Northern blot technique at the level of the target nucleic acid, or by means of the Western blot technique at the protein level (cf., for example, Sambrook, J., Fritsch, E. F. and Maniatis, T.: "Molecular Cloning: A Laboratory Manual", 2nd Edition, Cold Spring Harbor Laboratory Press, 1989; the entire contents of this publication is hereby incorporated by reference). In this connection, the expression "hybridization" in particular denotes binding by way of hydrogen bonds, known as "Watson-Crick base-pairing", between complementary bases of an oligonucleotide derivative according to the invention, on the one hand, and of a target nucleic acid, on the other hand. Guanine and cytosine are an example of complementary bases between which three hydrogen bonds are formed. Adenine and thymine, or adenine and uracil, are examples of complementary bases between which two hydrogen bonds are formed in each case. "Specific hybridization" denotes that a sufficient degree of complementarity exists between the oligonucleotide derivative according to the invention and the target nucleic acid to enable specific binding between the oligonucleotide derivative and the nucleic acid to be achieved. In this context, it is not absolutely necessary, for achieving specific hybridization, for 100% complementarity to exist between the oligonucleotide derivative according to the invention and the target nucleic acid. An oligonucleotide derivative according to the invention hybridizes "specifically" with a target nucleic acid when the binding of the oligonucleotide to the target nucleic acid impairs the function of the latter and, furthermore, an adequate degree of complementarity is present in order to avoid non-specific binding of the oligonucleotide derivative according to the invention to a nucleic acid other than the target nucleic acid when specific binding is required, for example under physiological conditions in association with an in-vivo application, such as a therapeutic treatment.

Specific hybridization can be determined, for example, by means of an in-vitro hybridization assay between an oligonucleotide derivative according to the invention and a target nucleic acid. Appropriate reaction conditions are known (cf., for example, Sambrook, J., Fritsch, E. F. and Maniatis, T.: "Molecular Cloning: A Laboratory Manual", 2nd Edition, Cold Spring Harbor Laboratory Press, 1989, Vol.2, 9.47 to 9.58; the entire content of this publication is hereby incorporated by reference).

By means of selecting a suitable base sequence, an oligonucleotide derivative according to the invention can, in principle, be directed against any target nucleic acid of interest. The present invention can consequently be applied independently of a particular base sequence per se of the oligonucleotide derivative according to the invention and consequently independently of the underlying target nucleic acid.

The present invention is preferably applicable to an oligonucleotide which has been found to be capable of modulating the expression of a protein or of an RNA molecule. Such an oligonucleotide is then modified in accordance with the invention, as explained below, by way of example, with the aid of a preferred embodiment.

Antisense oligonucleotides which are directed against human c-raf RNA, in particular an antisense oligonucleotide which is complementary to the region which extends from base position 2484 to base position 2503 of human c-raf mRNA (in accordance with T. I. Bonner et al., Nucleic Acids Res. 14 (1986), 1009–1015), have already been described (B. P. Monia et al., Nature Medicine 2 (1996), 668–675; K.-H. Altmann et al., Chimia 50 (1996), 168–176). Within the context of the present invention, it was observed that such an antisense oligonucleotide (designated ISIS 5132 in the said publications of B. P. Monia et al. and K.-H. Altmann et al.) is particularly effective when it is present in a form which has been modified in accordance with the invention, i.e. when it exists as an oligonucleotide derivative in which at least one nucleoside building block of the said antisense oligonucleotide has been replaced by a nucleoside building block of the said formula (I).

Consequently, another preferred embodiment of the present invention relates to an oligonucleotide derivative according to the invention which is essentially complementary to the region which extends from base position 2484 to base position 2503 of human c-raf mRNA (in accordance with T. I. Bonner et al., Nucleic Acids Res. 14 (1986), 1009–1015). The base sequence of the nucleoside building blocks of the said region of human c-raf mRNA is

5'-AAUGCAUGUCACAGGCGGGA-3' (SEQ.ID.NO.1).

Within the context of the present invention, "essentially complementary" denotes that the oligonucleotide derivative according to the invention possesses a sufficiently high complementarity to the target strand so that it is capable of hybridizing specifically with the said region of human c-raf mRNA.

However, an oligonucleotide derivative according to the invention whose base sequence possesses one or more, for example 1, 2 or 3, base mispairings ("mismatches") in relation to the base sequence of the said region of the target nucleic acid c-raf mRNA is also regarded, within the context of the present invention, as being "essentially complementary" to the target nucleic acid as long as such an oligonucleotide derivative is able to hybridize specifically with the said region of the target nucleic acid.

Particularly preferably, the oligonucleotide derivative according to the invention has the following base sequence

5'-TCCCGCCTGTGACATGCATT-3' (SEQ.ID.NO.2)

or a base sequence which is analogous thereto, with the oligonucleotide derivative comprising at least one nucleotide building block which corresponds to the said formula (I). Such an oligonucleotide consequently consitutes another preferred part of the subject-matter of the present invention. Within the context of the present invention, "analogous base sequence" denotes a base sequence in which one or more nucleic acid bases of the base sequence according to SEQ.ID.NO.2 has/have been replaced by corresponding analogous nucleic acid bases, for example cytosine by 5-methylcytosine, or adenine by 2-aminoadenine, or by an inert base like hypoxanthine. Such analogous or inert bases are known to the skilled person and are mentioned above.

The length of such an oligonucleotide derivative according to the invention preferably corresponds to the length of the said region of human c-raf mRNA, that is to 20 nucleoside building blocks.

Those oligonucleotide derivatives which are directed against c-raf mRNA are further preferred which correspond to the particular and preferred embodiments, which are mentioned herein, of the oligonucleotide derivatives according to the invention, in particular those which possess additional modifications and/or a chimeric structure.

Preferably, such an oligonucleotide derivative according to the invention is able to modulate expression of the human c-raf protein.

The invention furthermore relates to a pharmaceutical composition which comprises an oligonucleotide derivative according to the invention, or a pharmaceutically tolerated salt thereof, in a pharmaceutically effective quantity, if desired together with a pharmaceutically tolerated excipient and/or auxiliary substance. Pharmaceutical compositions according to the invention (and also oligonucleotide derivatives according to the invention) can be used, for example, for the therapeutic or prophylactic treatment of hyperplastic or neoplastic states, for example cancer or restenosis.

Pharmaceutical compositions which are preferred in accordance with the invention comprise preferred oligonucleotide derivatives as described above.

The pharmaceutical compositions according to the invention are preferably present in the form of preparations which can be administered parenterally or of infusion solutions. Aqueous solutions of the active substance in water-soluble form, for example in the form of one of the abovementioned water-soluble salts, in the presence or absence of salts, such as NaCl, and/or pharmaceutically tolerated excipient materials, such as sugar alcohols, for example mannitol, are suitable, in particular, for parenteral administration, for example for intravenous or intraperitoneal administration. Aqueous suspensions for injection which comprise viscosity-increasing substances, such as sodium carboxymethyl cellulose, sorbitol and/or dextran, are also suitable for parenteral administration. These preparations or solutions are preferably isotonic aqueous solutions or suspensions. The active substance can be present, for example, in the form of a lyophilisate, if necessary together with a pharmaceutically tolerated excipient material, which lyophilisate is brought into solution, before its use for parenteral administration, by adding a suitable solvent. These solutions which are suitable for parenteral administration can also be employed as infusion solutions. The pharmaceutical compositions according to the invention can be sterilized and/or comprise auxiliary substances, for example preservatives, stabilizers, wetting agents and/or emulsifying agents, solubilizing agents, salts for regulating the osmotic pressure and/or buffers.

The pharmaceutical preparations, which, if desired, can comprise additional pharmacologically (or pharmaceutically) active compounds, for example antibiotics, are prepared in a manner known per se, for example by means of conventional solubilizing or lyophilizing methods, and comprise from about 0.0001% by weight to about 95% by weight, preferably from about 0.1% by weight, to about 90% by weight, in particular from about 0.5% by weight to about 30% by weight, for example from 1% by weight to 5% by weight, of active compound(s). Dosage forms in the form of individual doses comprise, for example, from about 0.001% by weight to about 20% by weight, of active compound(s); dosage forms which are not in the form of individual doses comprise, for example, from about 0.001% by weight to about 10% by weight of active compound(s). Dose units preferably comprise from about 0.0005 mg to about 0.5 mg, preferably from about 0.005 mg to about 40 mg of active compound(s), depending on the nature of the mammalian subject, including man, to be treated, on the disease to be treated and on the condition of the patient, in particular its/his/her body weight, its/his/her age and its/his/her individual state of health, and also on individual pharmacokinetics contributing factors and the route of administration.

In order to improve activity, the pharmaceutical compositions according to the invention can comprise cationic lipids.

Pharmaceutical compositions according to the invention are also preferred which additionally comprise a customary cytostatic agent. Such combination preparations are preferably employed for treating hyperplastic or neoplastic states such as cancer.

The present invention furthermore relates to an oligonucleotide derivative according to the invention, including the abovementioned preferences, or a pharmaceutically tolerated salt thereof, for use in the prophylactic or therapeutic treatment of a mammalian subject including man.

The present invention furthermore relates to the use of an oligonucleotide derivative according to the invention, including the abovementioned preferences, or of a pharmaceutically tolerated salt thereof, for preparing a pharmaceutical composition for the prophylactic or therapeutic treatment of a pathological state in a mammalian subject, including man, which is characterized by the expression of a protein or an RNA molecule.

Over and above this, the present invention relates to a process for the prophylactic or therapeutic treatment of a pathological state in a mammalian subject, including man, which state is characterized by the expression of a protein or an RNA molecule, which comprises administering a pharmaceutical composition according to the invention to the mammalian subject.

Moreover, the invention relates to a process for modulating the expression of a protein or an RNA molecule in a cell, which comprises bringing the cell, or a tissue or body fluid which contains this cell, into contact with an oligonucleotide derivative according to the invention, including the abovementioned preferences, or with a pharmaceutical composition according to the invention. Such a process for modulating the expression of a protein or an RNA molecule in a cell can be advantageously applied both in vitro and in vivo.

The oligonucleotide derivatives according to the invention, including the abovementioned preferences, are also suitable for use as diagnostic agents and can be employed, for example, in a manner known per se, as gene probes for detecting genetically determined diseases or viral infections by means of selective interaction at the level of single-stranded or double-stranded target nucleic acids. In particular, a diagnostic application is possible in vivo as well as in vitro, due to the increased stability towards nucleases. The diagnosis can take place, for example, on isolated tissue samples, blood plasma, blood serum or other body fluids, and, in the case of in-vivo diagnosis, on tissues, cells or body fluids in the patient to be investigated as well.

Another aspect of the present invention consequently relates to an oligonucleotide derivative according to the invention, including the abovementioned preferences, for use in a diagnostic method. As mentioned above, the oligonucleotide derivatives according to the invention are suitable both for in-vivo and for in-vitro diagnostic methods.

Compounds of the formula (Ia) according to the invention, including the preferred embodiments, can furthermore be employed as pharmaceutical active compounds, for example for the therapeutic or prophylactic treatment of infectious diseases, in particular of viral infectious diseases. Consequently, the invention also provides a compound of the formula (Ia) according to the invention, including the preferred embodiments, for use in the therapeutic treatment of a mammalian subject including man. The invention also provides a pharmaceutical composition which comprises a therapeutically effective quantity of a compound of the formula (Ia) according to the invention, including the said preferences, or a pharmaceutically tolerated salt thereof, if necessary together with a pharmaceutically tolerated excipient and/or auxiliary substance.

It is to note that the entire content of the references, patents and publications cited in this application is hereby incorporated by reference.

The following examples clarify the invention but do not restrict it. Examples are in particular directed to preferred embodiments of the present invention.

EXAMPLES

The $^1$H NMR spectra are based on the numbering of the carbon atoms in the following cyclic carbon skeletons:

Starting compounds:

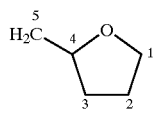

Nucleosides (Examples):

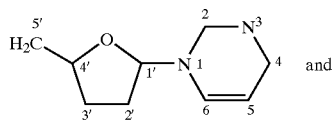

and

-continued

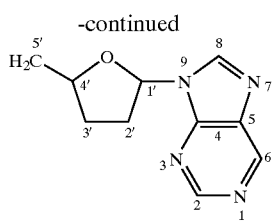

Abbreviations which are used in the text and in the formulae:

DMF dimethylformamide
TIPS-Cl$_2$ tetraisopropyldisiloxane dichloride
Bn benzyl
BOM-Cl benzyloxymethyl chloride
DMT-OTf 4,4'-dimethoxytrityl triflate
THF tetrahydrofuran
Cl$_2$Bn 2,4-dichlorobenzyl
Ms mesylate
z benzyl carbamate A) Preparation of Nucleoside Building Blocks According to the Invention Example A1

11.05 g of NaH (55% in oil) are added in several portions, at −5° C., to a solution of starting compound (E1) (obtainable according to W. T. Markiewicz, J. Chem. Research (S) (1979), p. 24, and P. Martin, Helv. Chimia Acta 8 (1995), pp. 486–504; the entire content of these publications is hereby incorporated by reference) in 850 ml of DMF. After 30 min., a further 5.8 g of NaH are added. After a further 30 min., 150 ml of a sat. solution of ammonium acetate are slowly added dropwise. Ethyl acetate (200 ml) and water (100 ml) are then added dropwise. The aqueous phase is extracted 3× with ethyl acetate.

The combined organic extracts are dried with MgSO$_4$ and concentrated by evaporation. The residue is recrystallized from hexane. The compound (A1) is obtained.

(E1)

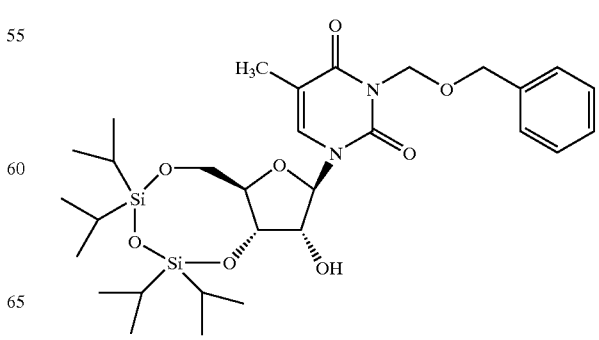

(A1)

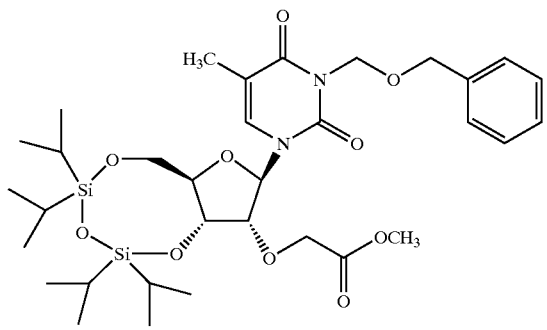

¹H NMR (250 MHz, CDCl₃): 7.55 [s, H—C(6)]; 7.2–7.4 [m, Ar.-Bom]; 5.75 [s, H—C(1')]; 5.5 [AB, C$\underline{H}_2$]; 4.7 [s, C$\underline{H}_2$]; 4.5 [dd, CH₂—OC(2')]; 3.7 [s, COOC$\underline{H}_3$]; 1.9 [s, CH₃(T)]; 1.0 [m. Tips]. MS: 693 (M+H)⁺.

Example A2

30 g of compound (A1) are dissolved in 430 ml of THF/methanol (8/2). The solution is cooled down to 5° C. 3.78 g of LiBH₄ are then added in small portions. After 30 minutes at 5° C., a sat. aqueous solution of NH₄Cl is added dropwise. The reaction mixture is then concentrated by evaporation and the residue subsequently diluted with 100 ml of water. After extraction with dichloromethane, the organic phase is dried with MgSO₄ and concentrated by evaporation. For removing salts, the residue is filtered through a small frit containing silica gel (ethyl acetate/hexane 4/6). The compound (A2) is obtained.

(A2)

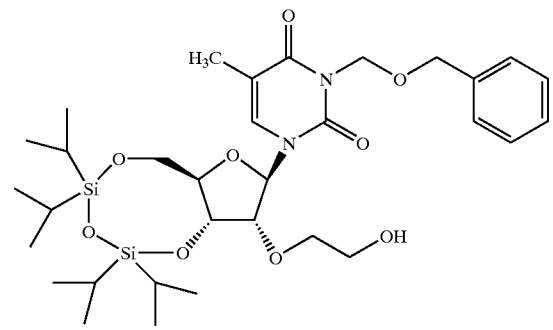

¹H NMR (250 MHz, CDCl₃): 7.55 [s, H—C(6)]; 7.2–7.4 [m, Ar.-Bom]; 5.7 [s, H—C(1')]; 5.5 [AB, C$\underline{H}_2$]; 4.7 [s, C$\underline{H}_2$]; 1.9 [s, CH₃(T)]; 1.0 [m, Tips]. MS: 665 (M+H)⁺.

Example A3

61 g of compound (A2) are dissolved in 1.5 l of dichloromethane. 35 ml of triethylamine, 45.7 g of tosyl chloride and 10 g of 4-dimethylaminopyridine are added at 20° C. The mixture is then stirred for 16 hours. The reaction mixture is extracted twice with 0.7 l of water and twice with a sat. aqueous solution of Na₂CO₃. The extract is dried with Na₂SO₄ and concentrated by evaporation. For purification, the residue is filtered rapidly through silica gel using hexane as eluent. The compound (A3) is obtained.

(A3)

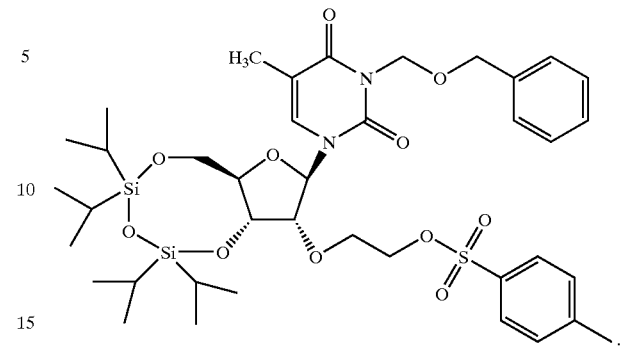

¹H NMR (250 MHz, CDCl₃): 7.8 [2H, tosyl]; 7.55 [s, H—C(6)]; 7.2–7.4 [m, 7H, tosyl+Ar.-Bom]; 5.6 [s, H—C(1')]; 5.5 [AB, Bom-C$\underline{H}_2$]; 4.7 [s, Bom-C$\underline{H}_2$]; 2.4[s, tosyl-CH₃; 1.9 [s, CH₃(T); 1.0 [m, Tips]. MS: 819 (M+H)⁺.

Example A4

30 g of compound (A3) are dissolved in 500 ml of DMF. The solution is cooled down to 0° C. Dimethylamine gas is then passed into the solution for 5 min. and the mixture is stirred in a sealed vessel at RT for 24 h. The reaction mixture is then poured onto water and this mixture is then extracted with ethyl acetate. The organic phase is dried with MgSO4 and concentrated by evaporation. The compound (A4) is obtained.

(A4)

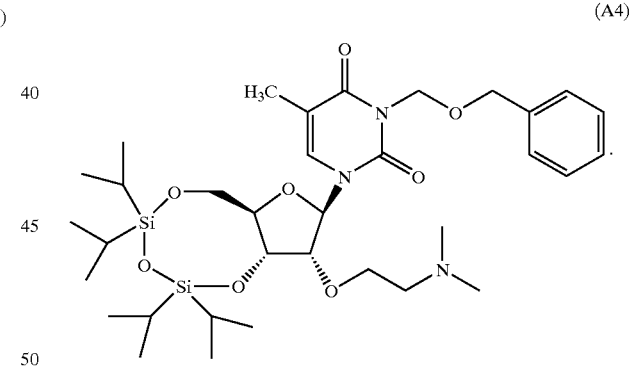

¹H NMR (250 MHz, CDCl₃): 7.55 [s, H—C(6)]; 7.2–7.4 [m, Ar.-Bom]; 5.7 [s, H—C(1')]; 5.5 [AB, Bom-C$\underline{H}_2$]; 4.7 [s, Bom-C$\underline{H}_2$]; 2.3[s, N(CH₃)₂]; 1.9 [s, CH₃(T)]; 1.0 [m, Tips]. MS: 692 (M+H)⁺.

Example A5

39.5 g of compound (A4) are dissolved in 700 ml of THF. 126 ml of a 1M solution of nBu₄NF in THF are added dropwise at room temperature and the reaction mixture is stirred at RT for 3 hours. Concentrating the solution by evaporation, and subsequent chromatography on silica gel (methanol/dichloromethane), yields compound (A5).

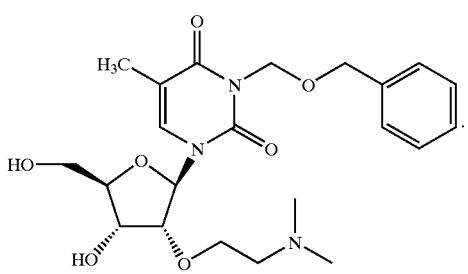

(A5)

¹H NMR (250 MHz, MeOH): 7.85 [s, H—C(6)]; 7.1–7.3 [m, Ar.-Bom]; 5.8 [d,H—C(1')]; 5.4 [s, Bom-CH₂]; 4.5 [s, Bom-CH₂]; 2.3[s, N(CH₃)₂]; 1.8 [s, CH₃(T)]. MS: 450 (M+H)⁺.

Example A6

21 g of compound (A5) are dissolved in 400 ml of methanol and hydrogenated over 2 g of Pd/C (10%) at 25° C. and under standard pressure for 3.5 hours. After filtration, the residue is extracted with a solution of NaHCO₃ and the organic phase is filtered through Hyflo Super Cel (from Fluka). The methanol is evaporated and the compound is dissolved in THF, and this solution is dried with Na₂SO₄ and concentrated by evaporation. The compound (A6) is obtained.

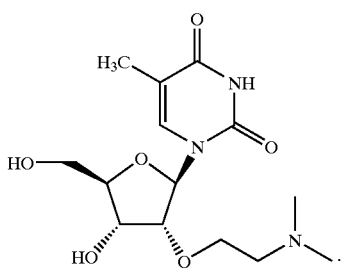

(A6)

¹H NMR (250 MHz, CDCl₃): 7.3 [s, H—C(6)]; 5.5 [d,H—C(1')]; 2.3[s, N(CH₃)₂]; 1.9 [s, CH₃(T)]. MS: 330 (M+H)⁺.

Example A7

1.08 g of compound (A6) are taken up twice in pyridine and concentrated by evaporation. The compound is taken up again in 20 ml of pyridine/dichloromethane (1/1) and 1.78 g of DMT-OTf are added. After having been stirred at room temperature for 1 hour, the reaction mixture is diluted with 20 ml of dichloromethane and the whole is poured onto 50 ml of NaHCO₃ solution. The organic phase is dried with Na₂SO₄ and concentrated by evaporation. The residue is chromatographed through silica gel (methanol/dichloromethane/triethylamine 9:89:2). The compound (A7) is obtained.

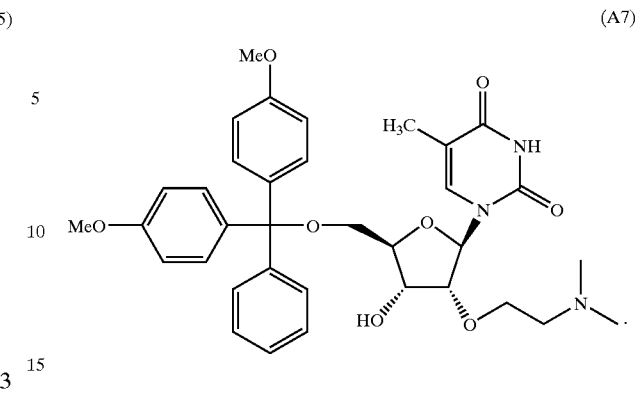

(A7)

¹H NMR (250 MHz, CDCl₃): 7.70 [s, H—C(6)]; 6.0 [d, H—C(1')]; 3.8 (s, OCH₃); 2.3 (s, CH₃); 1.4 (s, CH₃). MS: 632 (M+H)⁺.

Example A8

6.57 g of compound (A7) are added to an initially introduced mixture of 4.3 g of diuisopropylammonium tetrazolide, 6.9 g of 2-cyanoethyl-N N,N'-N'-tetraisopropyl-phosphorodiamidite and 30 ml of dichioromethane. The reaction mixture is stirred at 40° C. for 1 hour and then poured onto a s aturated aqueous solution of NaHCO₃. The organic phase is dried with Na₂SO₄ and concentrated by evaporation. The residue is chromatographed through silica gel (methanol/methylene chloride 5:95 containing 2% added triethylamine). The resulting foam is dissolved in 80 ml of ether and this solution is added dropwise, for precipitation, to pentane at 0° C. The compound (A8) (diastereoisomers, 1:1) is obtained.

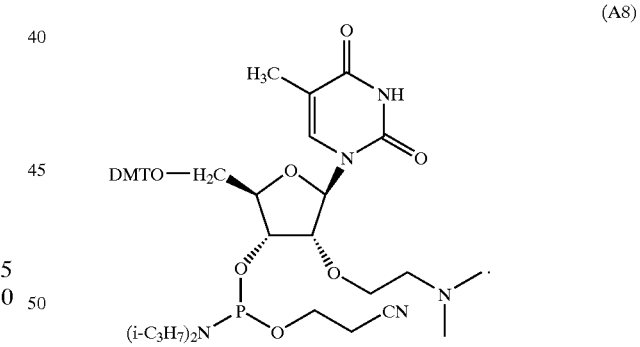

(A8)

¹H NMR (250 MHz, CDCl₃): 7.7 (s, H—C(6)] and 7.6 [s, H—C,(6)]; 6.1 [d, H—C(1)]; 6.0 [d, H—C(1')]; ³¹P NMR (CDCl₃): 150.186 and 150.012, MS: 832 (M+H)⁺.

Example A9

3.5 g of compound (A3) are slurried in 30 ml of dimethylformamide and the mixture is cooled down to 0° C. Gaseous methylamine is then passed in for 5 min., the reaction vessel is sealed, and the solution is stirred at RT for 3.5 hours. The reaction mixture is then poured onto water and this mixture is extracted with ethyl acetate. The organic phase is dried with MgSO₄ and concentrated by evaporation.

The compound (A9) is obtained.

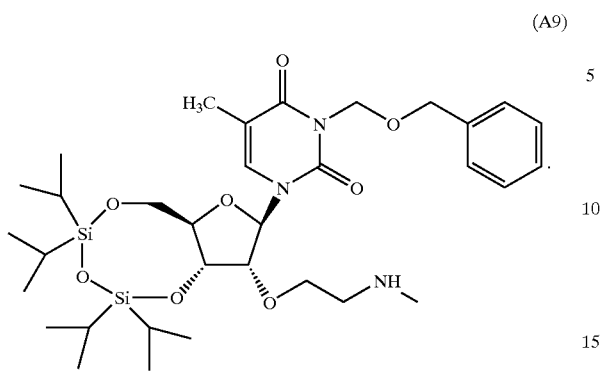

(A9)

$^1$H NMR (250 MHz, CDCl$_3$): 7.55 [s, H—C(6)]; 7.2–7.4 [m, Ar.-Bom]; 5.7 [s, H—C(1')]; 5.5 [AB, Bom-C$\underline{H}_2$]; 4.7 [s, Bom-C$\underline{H}_2$]; 2.45[s, NCH$_3$; 1.9 [s, CH$_3$(T)]; 1.0 [m, Tips]. MS: 678 (M+H)$^+$.

Example A10

2.63 g of compound (A9) are dissolved in 30 ml of pyridine and the solution is cooled down to 0° C. 0.6 ml of trifluoroacetic anhydride is then added dropwise and the mixture is stirred at 23° C. for 1 h. The reaction mixture is then concentrated by evaporation and the residue is taken up in ethyl acetate; the solution is extracted three times with water and then dried with Na$_2$SO$_4$ and concentrated by evaporation. The compound (A10) is obtained after concentrating by evaporation and then chromatographing the residue on silica gel (ethyl acetate/hexane 3/7).

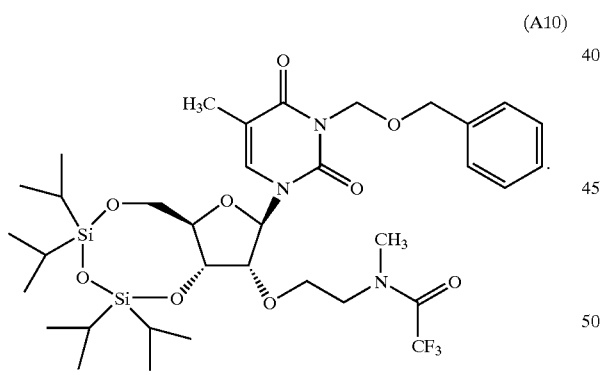

(A10)

$^1$H NMR (250 MHz, CDCl$_3$, 2 rotamers): 7.55 [2s, H—C(6)]; 7.2–7.4 [m, Ar.-Bom]; 5.7 [2s, H—C(1')]; 5.5 [AB, Bom-C$\underline{H}_2$]; 4.7 [s, Bom-C$\underline{H}_2$]; 3.2 [2s, NCH$_3$]; 1.9 [s, CH$_3$(T)]; 1.0 [m, Tips]. $^{19}$F NMR (CDCl$_3$): −68.75–70.38 (2s, C$\underline{F}_3$). MS: 774 (M+H)$^+$.

Example A11

Compound (A10) is converted into the phosphoramidite (A11) (diastereoisomers, 1:1; 2 rotamers in each case) in analogy with the protocols described in Examples A5, A6, A7 and A8.

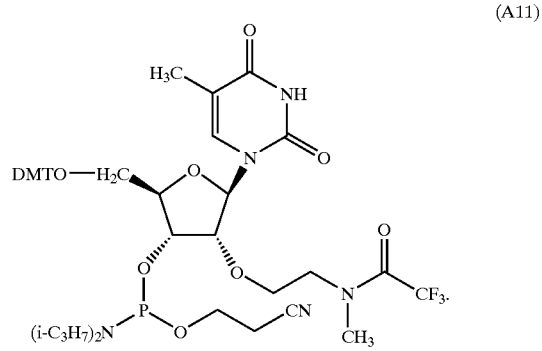

(A11)

$^1$H NMR (250 MHz, CDCl$_3$): 7.7 [2d, $\underline{H}$—C(6)]; 6.1 [2dd, $\underline{H}$—C(1)]; 3.2 [2dd, NCH$_3$]; $^{31}$P NMR(CDCl$_3$): 150.346 150.246 150.053 and 149.671 [2d]; $^{19}$F NMR (CDCl$_3$): −68.60 −68.67 −70.24 (C$\underline{F}_3$). MS: 914 (M+H)$^+$.

Example A12

6.0 g of compound (A3) are dissolved in 30 ml of DMF. After adding 1.43 g of sodium azide, the mixture is stirred at 65° C. for 2 hours. The reaction mixture is then diluted with 50 ml of ethyl acetate and the whole is poured onto 50 ml of water. The organic phase is dried with Na$_2$SO$_4$ and concentrated. The compound (A12) is obtained.

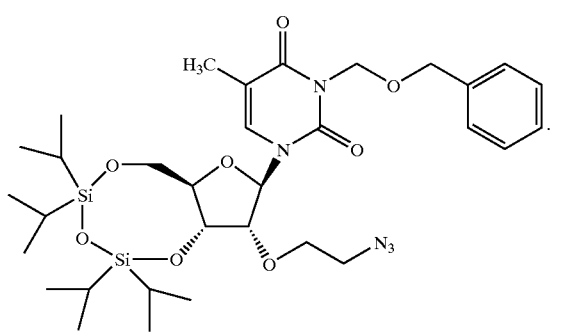

(A12)

$^1$H NMR (250 MHz, CDCl$_3$): 7.6 [s, H—C(6)]; 7.2–7.4 [m, Ar.-Bom]; 5.7 [s, H—C(1')]; 5.5 [AB, Bom-C$\underline{H}_2$]; 4.7 [s, Bom-C$\underline{H}_2$]; 1.9 [s, CH$_3$M)]; 1.0 [m, Tips]. MS: 690 (M+H)$^+$.

Example A13

4.8 g of compound (A12) are dissolved in 20 ml of methanol, and 3.96 g of solid SnCl$_2$ are added to this solution. The reaction mixture is stirred at room temperature for 3 hours and then poured onto a saturated aqueous solution of NaHCO$_3$. The methanol is evaporated and the residue is diluted with methylene chloride. The organic phase is filtered through Hyflo. After extracting with water, the organic phase is dried with MgSO4 and concentrated by evaporation. The residue is chromatographed through silica gel (methanol/methylene chloride, 1/9). The compound (A13) is obtained.

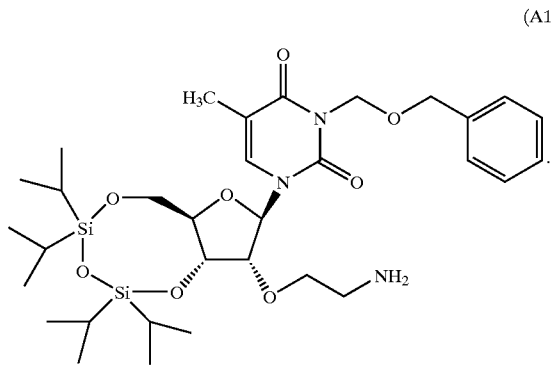

(A13)

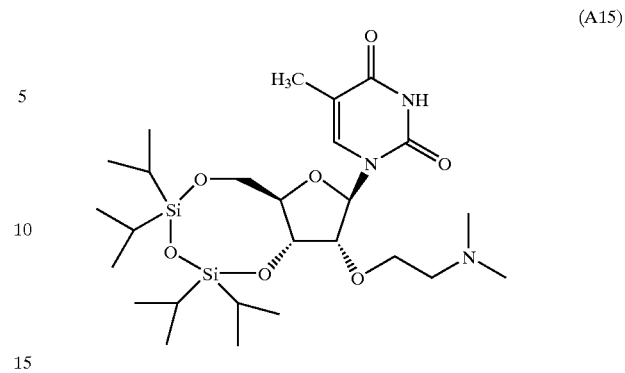

(A15)

¹H-NMR (250 MHz, CDCl₃): 7.55 [s, H—C(6)]; 7.2–7.4 [m, Ar.-Born]; 5.7 [s, H—C(1')]; 5.5 [AB, Bom-C$\underline{H}_2$]; 4.7 [s, Bom-C$\underline{H}_2$]; 2.6 [bd s, NH₂]; 1.9 [s, CH₃(T)]; 1.0 [m, Tips]. MS: 664 (M+H)⁺.

¹H NMR (250 MHz, CDCl₃): 7.6 [s, H—C(6)]; 5.7 [s, H—C(1')]; 1.9 [s, CH₃(T)]; 1.0 [m, Tips]. MS: 571 (M+H)⁺.

Example 14

Example A16

Compound (A13) is converted into the phosphoramidite (A14) (diastereoisomers, 1:1) in analogy with the protocols described in Examples A10, A5, A6, A7 and A8.

1.8 ml of POCl₃ are added slowly to a solution of 12.23 g of triazole and 25.2 ml of triethylamine in 140 ml of methylene chloride/acetonitrile (1/1). After 30 minutes, a solution of 4.5 g of compound (A15) in 20 ml of methylene chloride/acetonitrile (1/1) is added dropwise. The reaction mixture is stirred at 17° C. for 2 hours and then concentrated by evaporation. The residue is extracted three times with 50 ml of water on each occasion and the organic phase is dried with MgSO₄. The compound (A16) is obtained after evaporating.

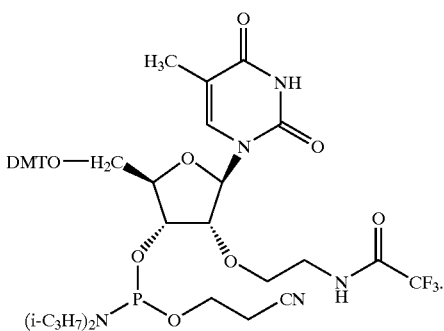

(A14)

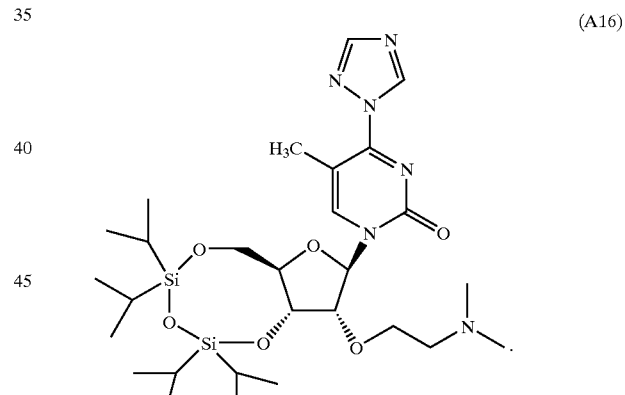

(A16)

¹H NMR (250 MHz, CDCl₃): 7.7 [2d, $\underline{H}$—C(6)]; 5.9 [m, $\underline{H}$—C(1)]; 3.8 [s, OCH₃]; ³¹P NMR(CDCl₃): 150.340 and 148.863; MS: 900 (M+H)⁺.

Example A15

3.5 g of compound (A6) are dissolved in 70 ml of pyridine, and 3.6 ml of Tips-Cl are added dropwise to the solution. The reaction mixture is stirred at 40° C. for 3 hours. After evaporating off the solvent, the residue is taken up in dichloromethanes the solution is washed with water and the organic phase is dried with MgSO₄ and concentrated by evaporation. The residue is chromatographed through silica gel (methanol/methylene chloride, 3/20). The compound (A15) is obtained.

¹H NMR (250 MHz, CDCl₃): 9.3 [s, triazolide]; 8.3 [s, $\underline{H}$—C(6)]; 8.1 [s, triazolide]; 5.8 [s, $\underline{H}$—C(1')]; 2.8 [m,NCH₂]; 2.5 [s, CH₃(T)]; 2.4 [s, N(CH₃)₂]; 1.0 [m, Tips]. MS: 623 (M+H)⁺.

Example A17

4.77 g of compound (A16) are dissolved in 100 ml of dioxane/conc. ammonia (3/7) and the solution is stirred at 20° C. for 3 hours. The reaction mixture is then concentrated by evaporation and the residue is dissolved in THF. The crude compound (A17) is obtained after drying (MgSO₄) and concentrating by evaporation.

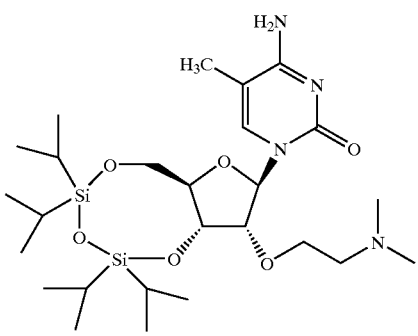

(A17)

MS:571 (M+H)⁺.

Example A18

2.17 g of compound (A17) are dissolved in 12 ml of pyridine and 0.75 g of benzoyl chloride is added dropwise. The reaction mixture is stirred at 55° C. for 3 hours and concentrated by evaporation, and the residue is treated with a mixture of water and methylene chloride. The organic phase is dried with MgSO₄ and concentrated by evaporation. Chromatography on silica gel (methanol/methylene chloride 5/95) yields the compound (A18).

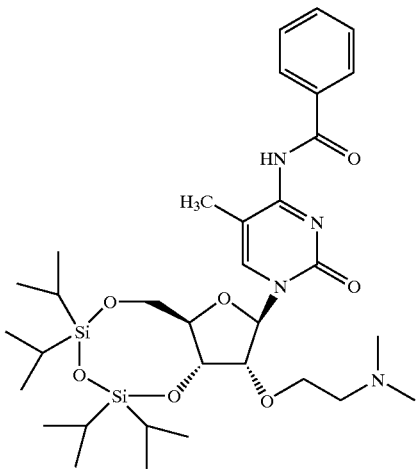

(A18)

¹H NMR (CDCl₃): 8.3 [d, benzyl]; 7.8 [s, H—C(6)]; 7.55 [t, benzyl]; 7.45 [t,benzyl] 5.7 [H—C(1')]; 2.45 [s, N(CH₃)₂]; 2.1 [s, CH₃(T)]; 1.0 [m, tips]. MS: 675 (M+H)⁺.

Example A19

Compound (A18) is converted into the phosphoramidite (A19) (diastereoisomers, 1:1) in analogy with the protocols described in Examples A5, A7 and A8.

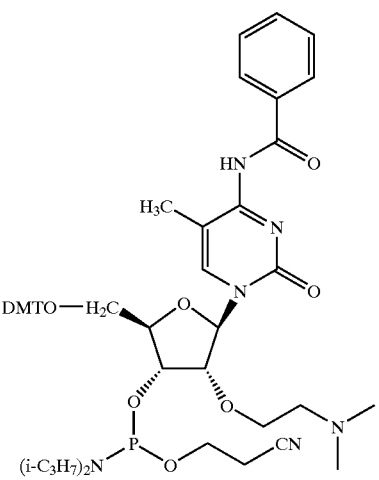

(A19)

¹H NMR (250 MHz, CDCl₃): 8.3 [d, benzoyl]; 7.9 [2s, H—C(6)]; 6.05 [2d, H—C(1); 2.3 [2d, N(CH₃)₂]; 1.5 [s, CH₃(T)]. ³¹P NMR(CDCl₃): 151.438.

Example A20

The starting compound (E2), obtainable in accordance with W. T. Markiewicz, see above, is converted into the product (A20) in analogy with the protocols described in Examples A1 and A2.

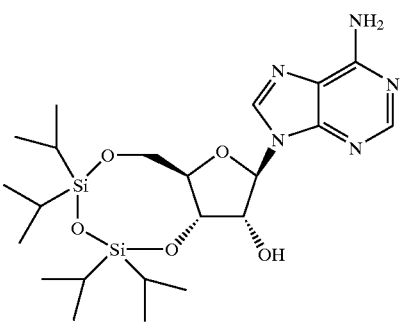

(E2)

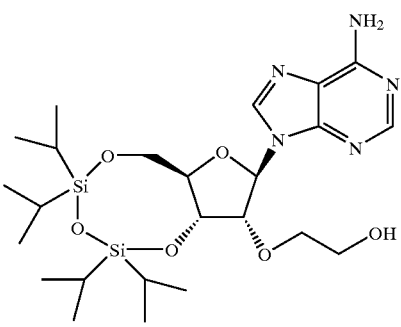

(A20)

¹H NMR (250 MHz, CDCl₃): 8.3 [s, H—C(8)]; 8.1 [s, H—C(2)]; 6.05 [s, H—C(1')]; 5.8 [bd s, NH₂]; 5.6 [m, H—C(3')]; 4.0 [m, CH₂—O); 3.8 [m, CH₂—O]; 1.0 [m, Tips]. MS: 554 (M+H)⁺.

Example A21

6.41 g of compound (A20) are dissolved in 210 ml of methanol, and 3.03 ml of N-methyl-2-dimethylpyrrolidine are added to this solution. The reaction mixture is stirred at 23° C. for 3 hours. After that, 6 ml of water are added and the solution is concentrated by evaporation. The residue is dissolved in methylene chloride and the solution is extracted three times with water. The organic phase is dried with MgSO$_4$ and concentrated by evaporation. The residue is chromatographed through silica gel (methanol/methylene chloride 7/93). The compound (A21) is obtained.

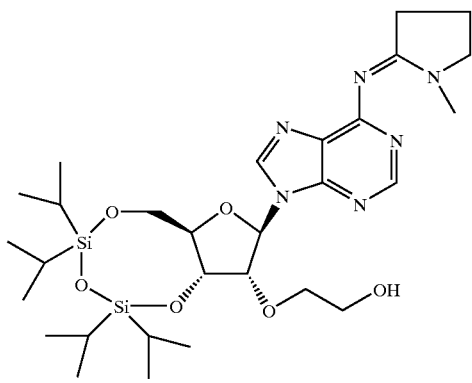

(A21)

$^1$H NMR (250 MHz, CDCl$_3$): 8.5 [s, H—C(8)]; 8.15 [s, H—C(2)]; 6.1 [s, H—C(1')]; 5.6 [M, H—C(3')]; 4.0 [m, CH$_2$—O]; 3.8 [m, CH$_2$—O]; 3.15 [s, CH$_3$N]; 1.0 [m, Tips]. MS: 635 (M+H)$^+$.

Example A22

Compound (A21) is converted into the phosphoramidite (A22) (diastereoisomers, 1:1) in analogy with the protocols described in Examples A3, A4, A5, A7 and A8.

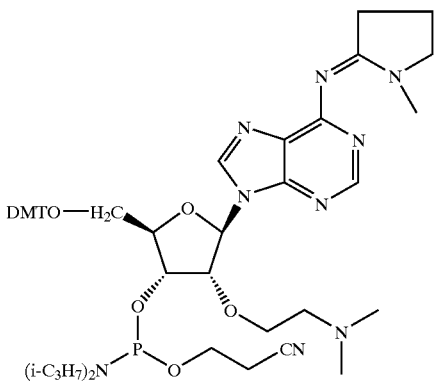

(A22)

$^1$H NMR (250 MHz, CDCl$_3$): 8.5 [2s, H—C(8)]; 8.15 [2s, H—C(2)]; 6.1 [m, H—C(1')]; 3.15 [s, CH$_3$N]; 1.0 [m, Tips]. $^{31}$P NMR(CDCl$_3$): 150.398 and 149.614; MS: 922 (M+H)$^+$.

Example A23

3.82 g of compound (A3) and 1.04 ml of N-methylpiperazine are dissolved in 20 ml of DMF and the solution is warmed to 40° C. After 3 hours, 1 ml of N-methylpiperazine is added to it. After a further 2.5 hours, the reaction mixture is concentrated by evaporation and the residue is then taken up in ether. After washing with water, the organic phase is dried with MgSO$_4$ and concentrated by evaporation. The residue is chromatographed through silica gel (methanol/methylene chloride 5/95). The compound (A23) is obtained.

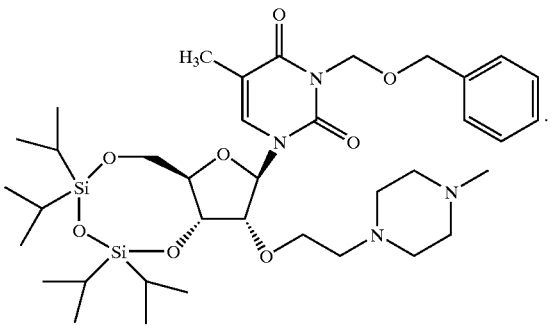

(A23)

$^1$H NMR (250 MHz, CDCl$_3$): 7.55 [s, H—C(6)]; 7.2–7.4 [m, Ar.-Bom]; 5.7 [s, H—C(1')]; 5.0 [AB, Bom-CH$_2$]; 4.7 [s, Bom-CH$_2$]; 2.3[s, NCH$_3$]; 1.9 [s, CH$_3$(T)]; 1.0 [m, Tips]. MS: 747 (M+H)$^+$.

Example A24

Compound (A23) is converted into the phosphoramidite (A24) (diastereoisomers, 1:1; 2 rotamers in each case) in analogy with the protocols described in Examples A5, A6, A7 and A8.

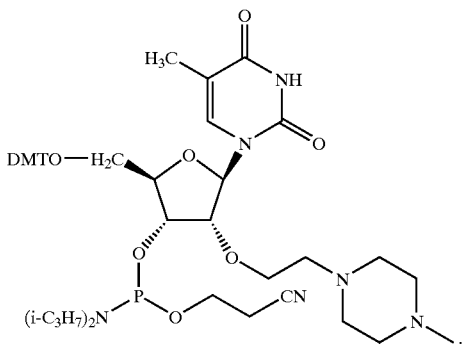

(A24)

$^1$H NMR (250 MHz, CDCl$_3$): 7.6 [2d, H—C(6)]; 6.0 [2dd, H—C(1)]; 2.3 [d, NCH$_3$]; $^{31}$P NMR(CDCl$_3$): 151.988; 151.805. MS: 887 (M+H)$^+$.

Example A25

6.63 g of compound (A3) and 4 ml of 3-dimethylamino-1-propylamine are dissolved in 80 ml of DMF and the solution is warmed to 40° C. After 24 hours, the reaction mixture is concentrated by evaporation. The residue is chromatographed through silica gel (methanol/methylene chloride/triethylamine 5/94/1 to 15/84/1). The compound (A25) is obtained.

(A25)

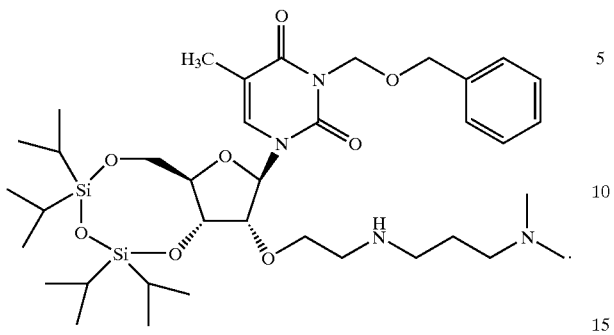

¹H NMR (250 MHz, CDCl₃): 7.5 [s, H—C(6)]; 7.2–7.4 [m, Ar.-Bom]; 5.65 [s, H—C(1')]; 5.45 [AB, Bom-C$\underline{H}_2$]; 4.7 [s, Bom-C$\underline{H}_2$]; 2.3[d, N(CH₃)₂]; 1.9 [s, CH₃(T)]; 1.0 m, Tips]. MS: 749 (M+H)⁺.

Example A26

Compound (A25) is converted into the phosphoramidite (A26) (diastereoisomers, 1:1; 2 rotamers in each case) in analogy with the protocols described in Examples A10, A5, A6, A7 and A8.

(A26)

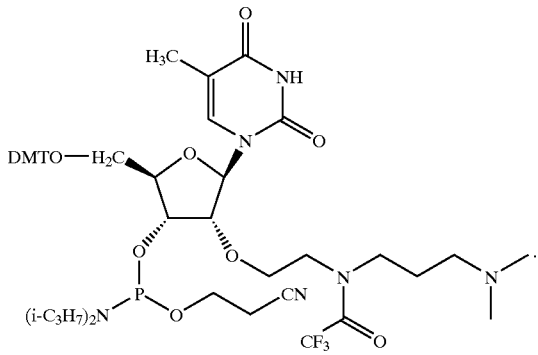

¹H NMR (250 MHz, CDCl₃): 7.7 [2d, $\underline{H}$—C(6)]; 6.0 [2dd, $\underline{H}$—C(1')]; 2.3 [2dd, N(CH₃)₂]; ³¹P NMR(CDCl₃): 151.594; 151.520; 151.473; 151.143. ¹⁹F NMR (CDCl): –68.940; –69.019; –69.523; –69.555 (2d, C$\underline{F}_3$). MS: 985 (M+H)⁺.

Example A27

38 mg of NaH (55% in oil) are added, in several portions, to a solution of 500 mg of starting compound (E3), which can be obtained in accordance with P. Martin, Helv. Chimica Acta 78 (1995), 486 (the entire content of this publication is hereby incorporated by reference), in 20 ml of THF. After 30 min. at 70° C., the reaction mixture is cooled down to 20° C. After that, 270 mg of (E4), which can be obtained in accordance with G. T. Anderson et al. J. Org. Chem. 61 (1996), 125 (the entire content of this publication is hereby incorporated by reference), are added dropwise and the reaction mixture is stirred at 80° C. After 24 hours, ethyl acetate and water are added dropwise. The aqueous phase is extracted 2× with ethyl acetate. The combined organic extracts are dried with MgSO₄ and concentrated by evaporation. The compound (A27) is obtained after chromatography through silica gel (ethyl acetate/hexane 3/7).

¹H NMR (250 MHz, CDCl₃; two rotamers): 7.6 [d, H—C(6)]; 7.2–7.4 [m, Ar]; 5.8–6 [d, H—C(1')]; 5.45 [AB, Bom-C$\underline{H}_2$]; 4.9–5.1 [2d, C$\underline{H}_2$ (Z)]. MS: 914 (M+H)⁺.

(E3)

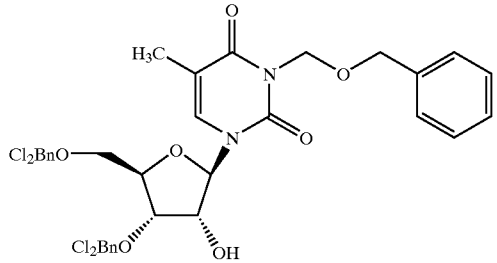

(E4)

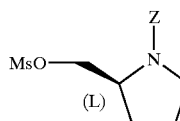

(A27)

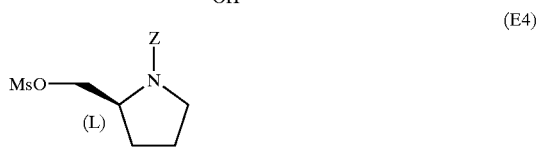

Example A28

300 mg of compound (A27) are dissolved in 20 ml of methanol/THF (1/1) and hydrogenated over 60 mg of Pd/C (20%), at 25° C. and under standard pressure, overnight. 1 eq. (330 µL, 1 N) of HCl is added dropwise to the reaction mixture, which is left to stir for 2 hours. After filtration, the residue is washed with a solution of NaHCO₃ and the organic phase is filtered through Hyflo. The filtrate is concentrated by evaporation and the residue is dissolved in THF; this solution is dried with Na₂SO₄ and concentrated by evaporation. The compound (A28) is obtained.

(A28)

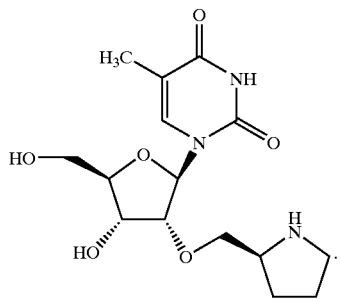

¹H NMR (250 MHz, CD₃OD): 7.8 [d, H—C(6)]; 5.8 [d, H—C(1')]; 4.3[m, H—C(3')]; 1.8 [s, CH₃(T)]; MS: 342 (M+H)⁺.

Example A29

The starting compound (E5), which can be obtained in accordance with W. T. Markiewicz, see above, is converted into the product (A29) in analogy with the protocols described in Examples A1, A2, A3 and A4.

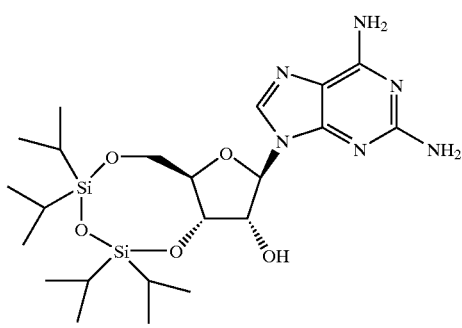
(E5)

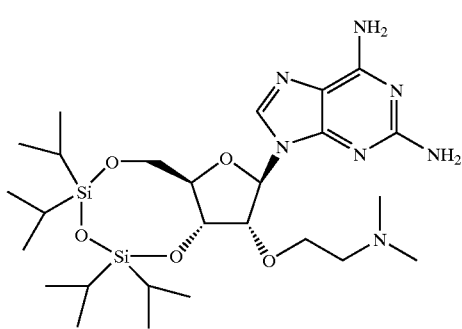
(A29)

$^1$H NMR (250 MHz, CDCl$_3$): 7.8 [s, H—C(8)]; 5.9 [s, H—C(1')]; 5.5 [bd s, NH$_2$]; 4.75 [bd s, NH$_2$]; 4.6 [m, H—C(3')]; 2.6 [t, CH$_2$—N]; 2.3 [s, N(CH$_3$)$_2$]; 1.0 [m, Tips]. MS: 596 (M+H)$^+$.

Example A30

Compound (A29) is converted into the product (A30) in analogy with the protocols described in Example A5.

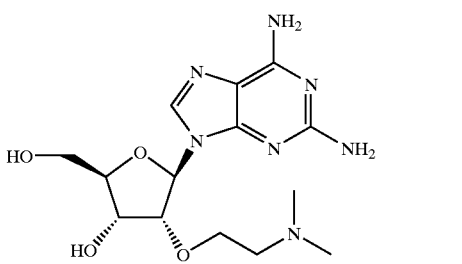
(A30)

$^1$H NMR (250 MHz, D$_2$O): 7.9 [s, H—C(8)]; 5.9 [d, H—C(1')]; 4.6 [m, H—C(3')]; 2.5 [t, CH$_2$—N]; 2.3 s, N(CH$_3$)$_2$]. MS: 354 (M+H)$^+$.

Example A31

2.76 g of compound (A30) are dissolved in 48 ml of phosphate buffer (pH 7) and 24 ml of methanol, and 1000 units of adenosine deaminase are added to this solution. The reaction mixture is stirred at 23° C. for 6 days with the pH being kept constant at 7 and a further 1000 units of deaminase being added each day. Methanol and half of the water are evaporated off. The residue is transferred into methanol; this mixture is then filtered. The compound (A31) is obtained after drying.

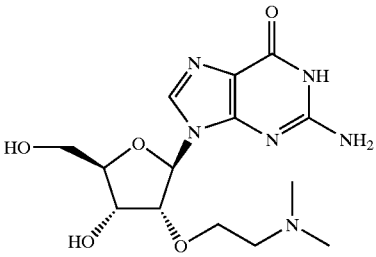
(A31)

$^1$H NMR (250 MHz, DMSO): 7.9 [s, H—C(8)]; 5.75 [d, H—C(1')]; 4.3 [m, H—C(2')]; 4.25 [m, H—C(3')]; 3.9 [m, H—C(4')]; 3.5–3.6 [m, 2H—C(5')]; 2.3 [s, N(CH$_3$)$_2$]. MS: 355 (M+H)$^+$.

Example A32

2.51 g of compound (A31) are suspended in 130 ml of methanol. After 4.7 ml of N,N-dimethylformamide dimethyl acetal have been added, the mixture is stirred at 20° C. for 7 hours. The reaction mixture is then filtered and the organic phase is concentrated. The compound (A32) is obtained).

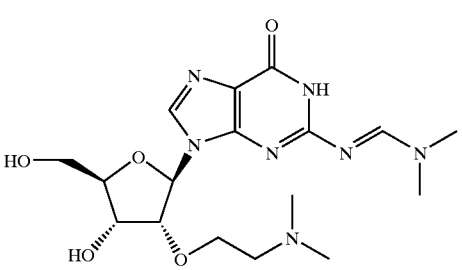
(A32)

Example A33

Compound (A32) is converted into the phosphoramidite (A33) (diastereoisomers, 1:1; 2 rotamers in each case) in analogy with the protocols described in Examples A7 and A8.

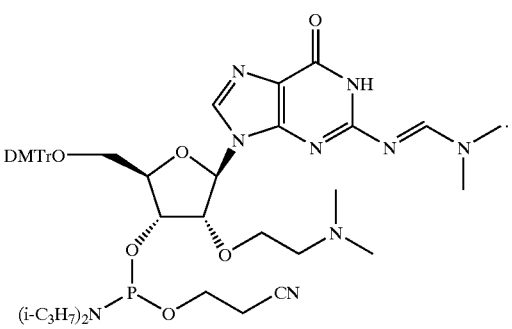
(A33)

$^1$H NMR (250 MHz, CDCl$_3$): 7.9 [d, H—C(8)]; 6.1 [2d, H—C(1')]; 2.3 [2s, N(CH$_3$)$_2$]. $^{31}$P NMR(CDCl$_3$): 151.658. MS: 912 (M+H)$^+$.

Example A34

1.53 g of compound (A29) are dissolved in 30 ml of dichloromethane/pyridine (1/1). 2.5 g of tertbutylphenoxyacetic anhydride and 31 mg of dimethylaminopyridine are added to this solution at 20° C. The mixture is then stirred for 24 hours. The reaction mixture is washed twice with water and twice with a sat. aqueous solution of Na$_2$CO$_3$ solution. The extract is dried with Na$_2$SO$_4$ and concentrated by evaporation. For purification, the residue is chromatographed through silica gel using methanol/dichloromethane (4/96) as the eluent. The compound (A34) is obtained.

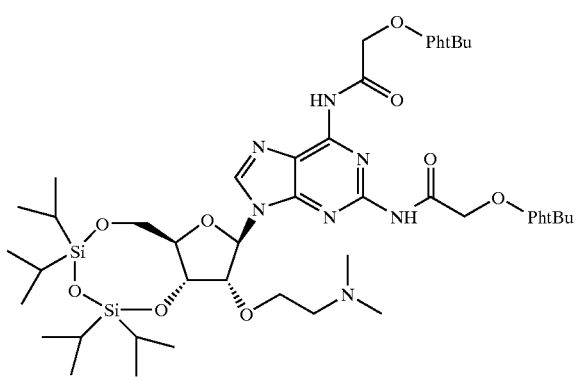

(A34)

$^1$H NMR (250 MHz, CDCl$_3$): 9.3 [bd s, CONH]; 9.0 [bd s, CONH]; 8,25 [s, H—C(8)]; 6.1 [s, H—C(1')]; 4.9 [bd s, CH$_2$CON]; 4.7 [bd s, CH$_2$CON]; 2.3 [s, N(CH$_3$)$_2$]; 1.0 [m, Tips]. MS: 976 (M+H)$^+$.

Example A35

Compound (A34) is converted into the phosphoramidite (A35) (diastereoisomers, 1:1; 2 rotamers in each case) in analogy with the protocols described in Examples A5, A7 and A8.

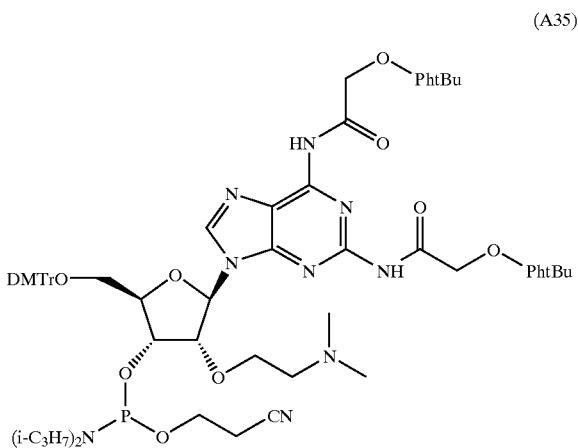

(A35)

$^1$H NMR (250 MHz, CDCl$_3$): 7.8 [d, H—C(8)]; 6.1 [2d, H—C(1')]; 2.2 [2s, N(CH$_3$)$_2$]. $^{31}$p NMR(CDCl$_3$): 151.630; 151.567. MS: 1236 (M+H)$^+$.

Example A36

1.42 9 of compound (A13) are dissolved in 50 ml of THF, and this solution is treated, at 0° C., with 4.7 ml of a 1 molar solution of tetrabutylammonium fluoride. After 2 hours, aqueous working-up takes place. The organic phase is dried with MgSO$_4$ and concentrated by evaporation. The residue is chromatographed through silica gel (methanol/methylene chloride 5/95). The compound (A36) is obtained.

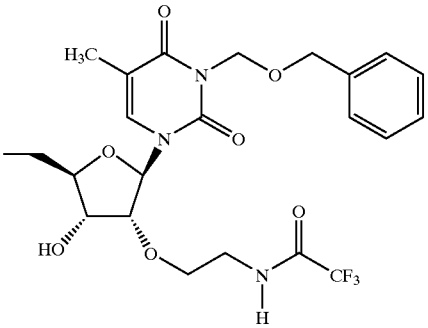

(A36)

$^1$H NMR (400 MHz, CDCl$_3$): 7.60 [s, H—C(6)]; 7.40–7.24 [m, 5H, BOM-Ar]; 5.75 [dd, H—C(1')]; 5.50 [s, 2H, BOM-CH$_2$]; 4.70 [s, 2H, BOM-CH$_2$]; 4.31 [m, H—C(3')]; 4.04 [m, 2H, H—C(2')]; 4.0–3.80 [m, H$_2$C(5')]; 3.7–3.47 (m, 4H, OCH$_2$CH$_2$N]; 3.02 [d, H—O(3')]; 2.53 [d, H—O (5')]; 1.92 [s, H$_3$C(T)]. $^{19}$F NMR (CDCl$_3$): –76.20; MS: 518 (M+H)$^+$.

Example A37

10.54 g of compound (A36) are dissolved in 100 ml of pyridine. 2.14 g of triphenylphosphine and 2.07 g of iodine are in each case added four times at intervals of 30 minutes and at RT. The reaction has ended after 6 hours at RT. The reaction mixture is diluted with ethyl acetate and this latter mixture is washed with a sat. solution of ammonium chloride. The combined organic phases are dried over Na$_2$SO$_4$ and concentrated by evaporation. The residue is chromatographed through silica gel (methanol/methylene chloride 5/95). The compound (A37) is obtained.

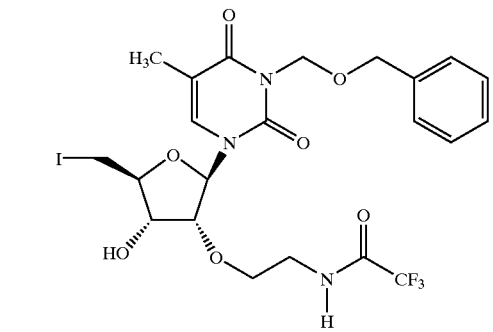

(A37)

$^1$H NMR (400 MHz, CDCl$_3$): 7.78 [t, H—N, NHCOCF$_3$]; 7.23–7.73 [m, H—C, 5H, (BOM-Ar) 7.55 [s, H—C(6)]; 5.80 [d, H—C(1')]; 5.50 [s, H—C, 2H, (BOM-CH$_2$)]; 4.70 [s, H—C, 2H (BOM-CH$_2$)]; 3.42–4.05 [m, H—C, 9H, H—C(2', 3', 4', 5', 5', CH$_2$CH$_2$)]; 1.95 (s, 3H, CH$_3$(T)]. MS:628 (M+H)$^+$.

Example A38

12.78 g of compound (A37) are dissolved in 100 ml of DMF, 1.99 g of sodium azide are added and the mixture is heated at 50° C. for 14 hours. The reaction mixture is cooled down to RT and diluted with ethyl acetate and this latter mixture is washed with a sat. solution of ammonium chloride. The combined organic phases are dried over Na$_2$SO$_4$ and concentrated by evaporation. The residue is chromatographed through silica gel (methanol/methylene chloride 5/95). The compound (A38) is obtained.

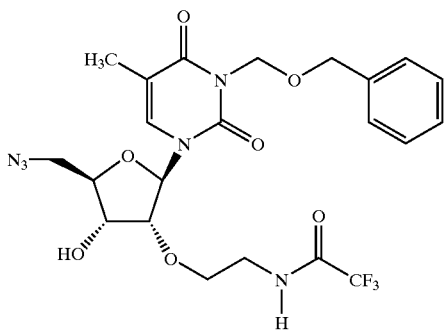

(A38)

¹H NMR (400 MHz, CDCl₃): 7.83 [t, H—N, NHCOCF₃]; 7.70–7.25 [m, H—C, 5H, (BOM-Ar)]; 7.45 [s, H—C(6)]; 5.79 [d, H—C(1')]; 5.50 [s, H—C, 2H, (BOM-CH₂)]; 4.70 [s, H—C, 2H (BOM-CH₂]; 3.83 [dd, H—C(2')]; 3.80 [dd, H—C(5')]; 3.60 [dd, H—C(5')]; 3.69–3.43 [m, 4H, OCH₂CH₂N]; 1.94 [s, 3H, CH₃(T)]; ¹⁹F NMR (CDCl₃): −76.09. MS:543 (M+H)⁺.

Example A39

10.74 g of compound (A38) are dissolved in 60 ml of methanol, and 2.1 g of palladium on charcoal (10%) are added to this solution. The mixture is stirred at room temperature and under an H₂ atmosphere. After 1 hour, the palladium catalyst is filtered off and the reaction mixture is concentrated. Compound (A39) is obtained.

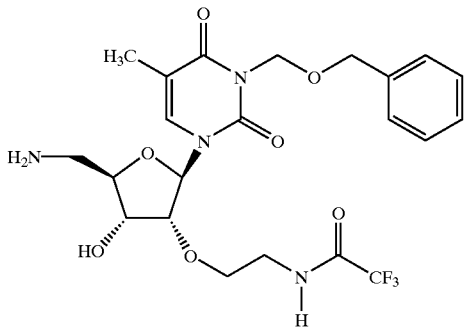

(A39)

¹H NMR (400 MHz, CD₃OD+CDCl₃): 7.47 [s, H—C(6)]; 7.35–7.20 [m, H—C, 5H, (BOM-Ar)]; 5.77 [d, H—C(1')]; 5.48 [s, H—C, 2H, (BOM-CH₂)]; 4.65 [s, H—C, 2H (BOM-CH₂)]; 4.08 [dd, H—C(3')]; 4.03 [dd, H—C(2')]; 3.90 [m, H—C(5')]; 3.90–3.43 [m, 4H, OCH₂CH₂N]; 3.08–2.87 (m, 2H, H₂C(5')]; 1.90 [s, 3H, CH₃(T)]; MS:517 (M+H)⁺.

Example A40

2.18 g of the carboxylic acid (E6), which can be obtained in accordance with A. De Mesmaeker et al., Angewandte Chemie 33 (1994), 226 (the entire content of this publication is hereby incorporated by reference), 1.75 g of compound (A39), 2.18 g of O-(benzotriazol-1-yl)-N,N,N',N'-tetramethyluronium tetrafluoroborate, 458 mg of N-hydroxybenzotriazole and 5.8 ml of N,N-diisopropyl-N-ethylamine are dissolved in 55 ml of N,N-dimethylformamide. The reaction mixture is stirred at room temperature for 16 h and then diluted with ethyl acetate and this latter mixture is washed with a sat. solution of ammonium chloride. The combined organic phases are dried over Na₂SO₄ and concentrated by evaporation. The residue is chromatographed through silica gel (methanol/methylene chloride 5/95). The compound (A40) is obtained.

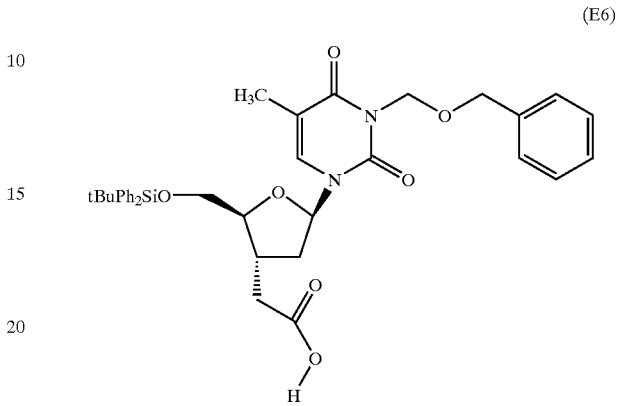

(E6)

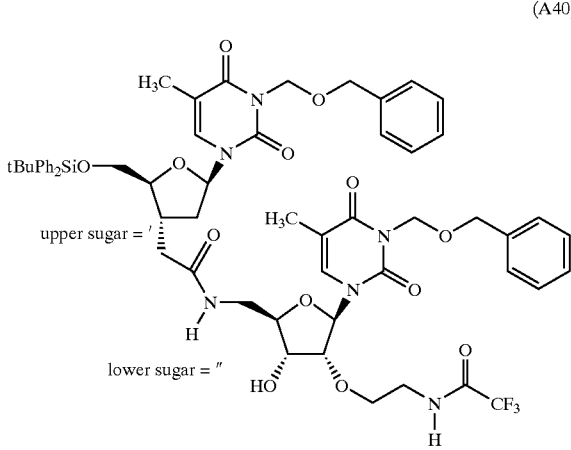

(A40)

¹H NMR (400 MHz, CDCl₃) (upper sugar=', lower sugar="): 7.97 [t, 1H, H-NCOCF₃]; 7.47 [s, H—C(6)]; 7.45–7.20 [m, 10H, BOM-Ar]; 7.10 [s, H—C(6)]; 6.7 [dt, H—N(5")]; 6.1 [dd, H—C(1')]; 5.49 [s, 4H, CH₂-BOM]; 4.66 [d, 4H, CH₂-BOM]; 4.23 [dd, H—C(2")]; 4.12 [m, H—C(3")]; 4.00 [m, H—C(4")]; 2.83 [m, H—C(3')]; 2.35–2.15 [m, 2H, H₂C(3')]; 1.94 (s, 3H, CH₃(T)]; 1.63 [s, 3H, CH₃(T)]. MS:1142 (M+H)⁺.

Example A41

3.87 9 of compound (A40) are dissolved in 50 ml of methanol. 2 ml of concentrated aqueous hydrochloric acid are added and the mixture is treated with 3.61 g of Pd-C (10%). After stirring for 16 hours at room temperature and under a hydrogen atmosphere, the palladium catalyst is filtered off. After the reaction mixture has been concentrated, the crude product is purified on silica gel (methanol/methylene chloride 15/85). The compound (A41) is obtained.

(A41)

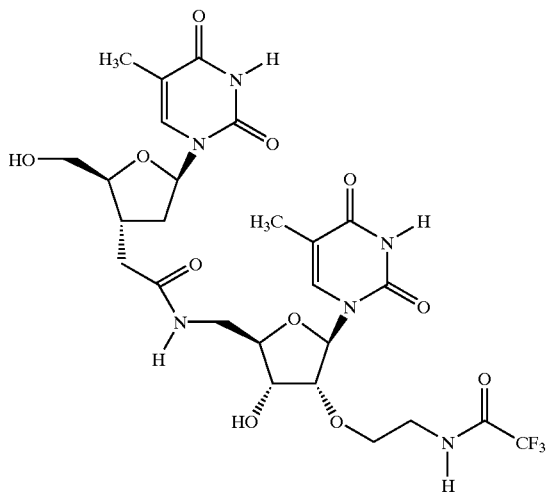

¹H NMR (400 MHz, CD₃OD): 8.00 [s H—C(6)]; 7.48 [s, H—C(6)]; 6.05 (dd, H—C(1'); 5.75 [d, H—C(1")]; 4.1 [dd, H—C(2")]; 3.9 [m, H—C(2')]; 2.7 [m, H—C(4")]; 2.5–2.15 [m, 2H, H₂C(3")]; 1.90 [d, 3H, CH₃(T)]; 1.88 [s, 3H, CH₃(T)]. MS: 664 (M+H)⁺.

Example A42

2.41 g of compound (A41) are dissolved in 15 ml of pyridine and the solution is treated with 1.48 g of dimethoxytrityl chloride. The reaction mixture is stirred at room temperature for 16 h and then diluted with ethyl acetate and this latter mixture is washed with a sat. solution of ammonium chloride. The combined organic phases are dried over NaSO₄ and concentrated by evaporation. The residue is chromatographed through silica gel (methanol/methylene chloride 10/90). The compound (A42) is obtained.

(A42)

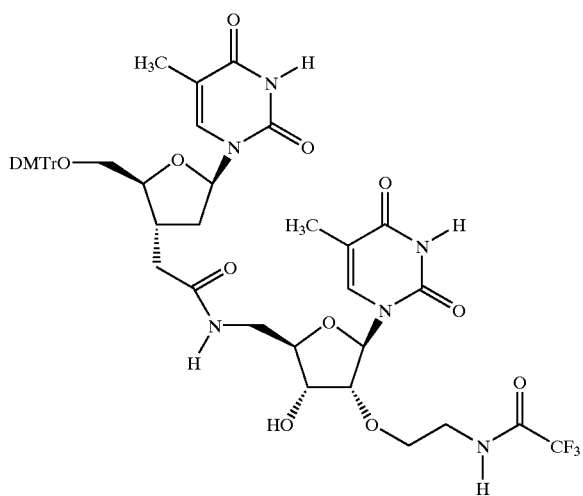

¹H NMR (400 MHz, CDCl₃): 7.68 [s, H—C(6)]; 7.11 [s, H—C(6)]; 7.45–6.8 [m, 13H, DMTr-Ar]; 6.10 [dd, H—C (1')]; 5.32 [d, H—C(1")]; 4.34 [dd, H—C(2")]; 4.25 [m, H—C(3")]; 3.78 [s, 6H, DMTr-OCH₃]; 2.90 [m, H—C(3')]; 2.40–2.17 [m, 2H, H—C (2')]; 1.90 [s, 3H, CH₃(T)]; 2.43 [s, 3H, CH₃(T)]. MS: 966 (M+H)⁺.

Example A43

552 mg of compound (A42) are dissolved in 12.5 ml of methylene chloride, and 259 mg of 2-cyanoethyl N,N,N',N'-tetraisopropylphosphorodiamidite and 196 mg of diisopropylammonium tetrazolide are added. The reaction mixture is stirred at room temperature for 16 h and then diluted with ethyl acetate and this latter mixture is washed with a sat. solution of sodium carbonate. The combined organic phases are dried over Na₂SO₄ and concentrated by evaporation. The residue is chromatographed through silica gel (ethyl acetate/tetrahydrofuran 3:1). The compound A(43) is obtained.

(A43)

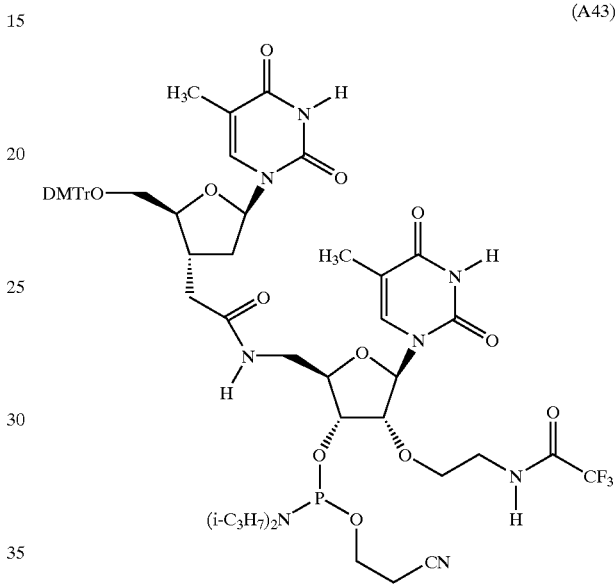

¹H NMR (400 MHz, CDCl₃): 7.65 [d, H—C(6)]; 7.08 [d, H—C(6)]; 7.45–6.8 [m, 13H, DMTr-Ar]; 6.10 [dd, H—C (1')]; 5.35 [d, H—C(1")]; 4.55 [dt, H—C(2")]; 4.25 [m, H—C(3")]; 1.90 [s, 3H, CH₃(T)]; 1.48 [s, 3H, CH₃(T)]. MS: 1166 (M+H)⁺.

Example B: Preparation of Oligonucleotide Derivatives According to the Invention Oligonucleotides are bonded to a solid support (controlled pore glass, CPG) using the novel 5'-dimethoxytritylated and 3'-activated [3'-(β-cyanoethoxy-di (i-propylamino) phosphoramidite)] nucleosides or nucleotide dimers, or such natural activated nucleosides, and the synthesis is carried out on a DNA synthesizer (Applied Biosystems, Model 380 B, standard phosphoramidite chemistry and iodoxidation) in accordance with the manufacturer's standard protocols (cf. also "Oligonucleotide Synthesis, A Practical Approach" M. J Gait; IRL Press 1984 (Oxford-Washington D.C.); the entire content of this publication is hereby incorporated by reference). If necessary, functional groups of the nucleosides which are used are protected in an appropriate manner. After the coupling of the last nucleoside building block, the 5'-protected oligonucleotide is released from the support, with the simultaneous elimination of all the remaining protecting groups, by treating with concentrated aqueous ammonia overnight, and subsequently purifying by means of reverse-phase HPLC using 50 mM ammonium acetate buffer (pH 7)/acetonitrile. The 5'-dimethoxytrityl protecting group is then eliminated by a 20-minute treatment with 80% aqueous acetic acid and the oligonucleotide is precipitated with ethanol and isolated by centrifugation. The purity of the oligonucleotide is examined by gel electrophoresis (polyacrylamide) and its identity is checked by means of matrix-assisted laser desorption time-of-flight mass spectroscopy (MALDI-TOF MS).

Example C: Properties of Oligonucleotide Derivatives According to the Invention

Example C1

Affinity; Interaction of Oligonucleotide Derivatives According to the Invention (as Antisense Oligonucleotides) with Complementary (Sense) Oligoribonucleotide Sequences The interaction of the oligonucleotides with the corresponding base-complementary oligomers of the natural ribonucleotides is characterized by plotting UV melting curves and by the $T_m$ values which are ascertained therefrom. This standard method is described, for example, in Marky, L. A., Breslauer, K. J., Biopolymers 26:1601–1620 (1987) (the entire content of this publication is hereby incorporated by reference).

A solution of the oligonucleotides and the corresponding base-complementary natural oligoribonucleotides is prepared in 10 mM phosphate buffer, 100 mM NaCl, 0.1 mM EDTA, pH=7.0 (c=4.10$^{-6}$ M/oligonucleotide) and the change in the extinction at 260 nm is plotted as a function of temperature (0° C. to 95° C.). The $T_m$ value, and from that the $\Delta$Tm(° C.)/modification (i.e. $\Delta$Tm per novel modified nucleoside building block) value, are determined from the resulting melting curves (Table 3; capital letters in the depicted sequences denote deoxyribonucleotides; lower case letters denote 2'-modified nucleoside building blocks; the depicted sequences only contain phosphodiester bonds).

TABLE 3

Affinity:

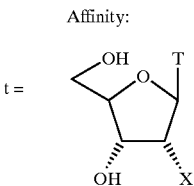

| X | Mass/calc. | /Exp. | Tm (° C.) | $\Delta$Tm (° C.)/Mod. |
|---|---|---|---|---|
| (a) 5'-TTTTtCTCTCTCTCT-3' (vs. RNA) (SEQ. ID. NO: 3) | | | | |
| H | | | 51.9 | 0 |
| O-CH₂CH₂-N(CH₃)₂ | 4511 | 4505 | 53.7 | +1.8 |
| O-CH₂CH₂-NHCH₃ | 4497 | 4493 | 53.7 | +1.8 |
| (b) 5'-TTTTtCtCtCtCtCT-3' (vs. RNA) (SEQ. ID. NO. 4) | | | | |
| H | | | 51.9 | 0 |
| O-CH₂CH₂-N(CH₃)₂ | 4859 | 4860 | 60.2 | +1.7 |
| O-CH₂CH₂-NHCH₃ | 4789 | 4787 | 59.3 | +1.5 |

TABLE 3-continued

Affinity:

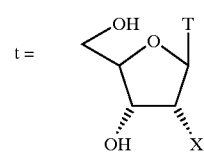

| X | Mass/calc. | /Exp. | Tm (° C.) | $\Delta$Tm (° C.)/Mod. |
|---|---|---|---|---|
| (c) 5'-tCCAGGtGtCCGCAtC-3' (vs. RNA) (SEQ. ID. NO. 5) | | | | |
| H | | | 61.7 | 0 |
| O-CH₂CH₂-N(CH₃)₂ | 5181 | 5180 | 66.7 | +1.2 |
| O-CH₂CH₂-NHCH₃ | 5126 | 5126 | 66.5 | +1.2 |

(d) Further examples of oligonucleotides which have been modified in accordance with the invention:

| Sequence type | Modification type | Mass calculated | Mass found | $\Delta$Tm(° C.)/mod |
|---|---|---|---|---|
| B | DMAE | 4859 | 4860 | +1.7 |
| C | DMAE | 4861 | 4853 | +0.7 |
| D | DMAE/MOE | 5301 | 5292 | +1.8 |
| E | DMAE | 5715 | 5714 | +0.37 |
| F | DMAE | 5367 | 5366 | +0.34 |
| C | MMAE | 4796 | 4784 | +0.36 |
| B | AE | 4721 | 4717 | +1.38 |
| C | AE | 4721 | 4723 | +0.5 |
| D | AE/MOE | 5161 | 5163 | +1.5 |
| B | APAE | 5137 | 5137 | +1.0 |
| C | APAE | 5137 | 5143 | +1.0 |
| B | PIPE | 5137 | 5132 | +2.0 |
| C | PIPE | 5137 | 5139 | +0.6 |
| G | DMAE | 4803 | 4806 | +0.8 |
| H | DMAE | 5151 | 5139 | +2.3 |
| I | DMAE | 5064 | 5068 | +1.0 |
| J | DMAE/MOE | 5448 | 5437 | +2.5 |
| K | DMAE | 5181 | 5180 | +1.2 |
| K | MMAE | 5126 | 5126 | +1.2 |

Clarification of Table (d):

Sequence Type

A: TTTTtCTCTCTCTCT (SEQ.ID.NO.3)

B: TTTTtCtCtCtCtCT (SEQ.ID.NO.4)

C: tttttCTCTCTCTCT (SEQ.ID.NO.6)

D: TTTTt<u>CtCtCtCtC</u>T C=2'1-MOE-$^{me}$C (SEQ.ID.NO.7)

E: tttttctctctctcT (SEQ.ID.NO.8)

F: TTTTtctctctctcT (SEQ.ID.NO.9)

G: AGAGAGAGAGaAAAA (SEQ.ID.NO.10)

H: AGaGaGaGaGaAAAA (SEQ.ID.NO.11)

I: AGAGAGAGAGaaaaA (SEQ.ID.NO.12)

J: A<u>GaGaGaGaGa</u>AAAA G=2'-MOE-G (SEQ.ID.NO.13)

K: AGGtGtCCGCAtC (SEQ.ID.NO.14)

Modification Type

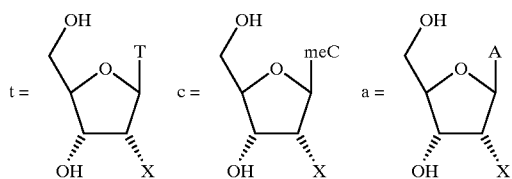

($^{me}$C: base=5-methylcytosine)

DMEA: X = O~N(CH₃)₂
2'-dimethylaminoethoxy

MMEA: X = O~NHCH₃
2'-monomethylaminoethoxy

AE: X = O~NH₂
2'-aminoethoxy

MOE: X = O~O~
2'-methoxyethoxy

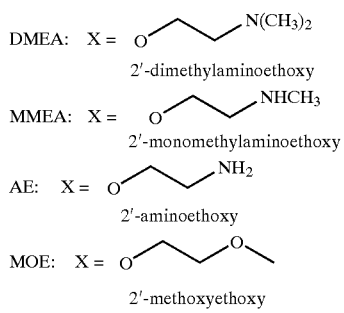

APAE: X =
2'-(3-N, N-dimethylamino-1-propyl) aminoethoxy

PIPE: X =
2'-piperazinethoxy

Example C2

Nuclease Resistance of Oligonucleotide Derivatives According to the Invention

The nuclease resistance of oligonucleotide derivatives according to the invention is investigated using snake venom phosphodiesterase (SVP), a non-specific endonuclease. For this, the oligonucleotides which are described below are labelled at the 5' end with $^{32}$P and incubated with SVP. The resulting digestion products are analyzed, in a customary manner, by means of polyacrylamide gel electrophoresis and quantified using a Molecular Dynamics Phosphorimager, and the respective half lives are determined (Table 4; capital letters in the depicted sequences denote deoxyribonucleotides; the depicted sequences only contain phosphodiester bonds).

Table 4 Nuclease Resistance (a) 5'-TCC AGG TGT CCG ttt C-3' (SEQ.ID.NO.15)

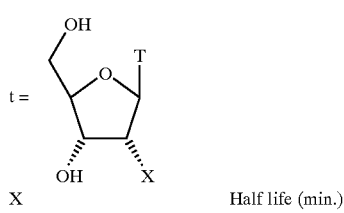

| X | Half life (min.) |
|---|---|
| H | 8.5 |
| O~N(CH₃)₂ | more than 1400 |
| O~NHCH₃ | more than 1400 |

Example C3

Affinity; Interaction of Oligonucleotide Derivatives According to the Invention (as Triplex-forming Oligonucleotides) with Double-stranded DNA The interaction of oligonucleotide derivatives according to the invention with the corresponding natural double-stranded DNA (target double strand) is determined, as a dissociation of the third strand from the double strand, by plotting UV melting curves (260 nm) in buffer (180 mM KCl, 10 mM PO4, pH 7.0, 20 mM Na+, 0.1 mM EDTA) and by means of the Tm values which are ascertained therefrom. The triplex-forming oligonucleotides and the double-stranded DNA which are used, and the ascertained Tm values, are presented in Table 5 (capital letters in the depicted sequences denote deoxyribonucleotides; the depicted sequences only contain phosphodiester bonds).

Table 5: Affinity (a) Target double strand (21-mer):

5'-d(GCTAAAAAGAGAGAGATCG)-3' (SEQ.ID.No.16)

3'-d(CGATTTTTCTCTCTCTAGC)-5' (SEQ.ID.NO.17)

(Tm of the target double strand: 62.4 +/−1.0° C.)

(b) Oligonucleotide sequence (third strand):

5α-TTTTtCtCtCtCT-3' (SEQ.ID.NO.4)

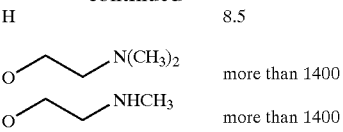

| X | Tm (° C.) (a) | ΔTm (° C.)/Mod. |
|---|---|---|
| H | 17.4 | 0 |
| O~N(CH₃)₂ | 28.7 | +2.24 |
| O~NHCH₃ | 35.6 | +3.62 |
| O~NH₂ | 35.2 | +3.56 |

Example C4

Inhibition of c-Raf Kinase mRNA in T24 Cells (i) Treatment of Cells in Culture with Antisense Oligonucleotides:

Cells growing on 10-cm plates at a density of 50–70% confluency are treated with the respective antisense oligonucleotides in the presence of cationic lipid(CL) (Lipofectin reagent, Gibco BRL). Alternatively, the electroporation technique is used (EP), as described in R. Griffey et al. J. Med. Chem. 39, 5100 (1996).

(ii) Northern blot analysis:

For determination of mRNA levels by northern blot, total RNA is prepared from cells by the guanidinium isothiocyanate procedure 24 h after initiation of antisense oligonucleotide treatment. Total RNA is isolated by centrifugation of the cell lysates over a cesium chloride cushion. After northern blot analysis, RNA is quantified and normalized to G3PDH mRNA levels, using a Molecular Dynamics Phosphorimager. The results are shown in Table 6.

Table 6: Sequence structure of tested oligonucleotides and $T_m$ and IC50 values (small bolded: DMAE-modification, see Example 3(d) above; underlined: MOE, see Example 3(d) above; o: phosphodiester linkage; s: phosphorothioate linkage; IC50: oligonucleotide concentration (nM) for 50% downregulation of the c-Raf mRNA; $T_m$: melting point, see Example 3 above)

| SEQ.ID. NO. | oligonucleotide structure | Tm (° C.) | IC50 (CL) | IC50 (EP) |
|---|---|---|---|---|
| 18 | TscsCscsGsCsTsGsTsGsAsCsAsts GscsAstsT | 66.4 | 200 | 350 |
| 19 | TocoCocoGoCsCsTsGsTsGsAsCsAsto GocoAotoT | 74.5 | 50 | 240 |
| 20 | tscscscsGsCsTsGsTsGsAsCsAsts GscsastsT | 66.4 | 50 | 200 |
| 21 | tocococoGoCsCsTsGsTsGsAsCsAsto GocoaotoT | 67.1 | 300 | 105 |
| 22 | TscsCscsGsCsTsGsTsGsAsCsAsts GscsAstsT | 68.6 | 50 | 230 |

Example C5

Antitumor Activity of Modified Antisense Oligonucleotides

Male Balb/c nu/nu mice (CIBA animal farm, Sisseln, Switzerland) are kept under sterile conditions with free access to food and water. For in vivo experiments, tumors are established after subcutaneous injection of cells (ATCC, Rockville, Md., USA) in carrier mice. The resulting tumors are serially passaged for a minimum of three consecutive transplantations prior to start of treatment. Fragments (approx. 25 mg) of the human lung adenocarcinoma A549 (ATCC No. CCL 185) are implanted s.c. into the left flank of animals with a 13-gauge trocar needle under Forene (Abbott, Switzerland) anaesthesia. Treatments are started when the tumor reaches a mean tumor volume of 100 to 150 mm³.

Tumor growth is monitored twice or three times weekly and 24 hours after the last treatment by measuring perpendicular diameters. Tumor volumes are calculated as previously described (Evans et al; Br. J. Cancer, 45: 466–468, 1982). The antisense oligonucleotides are administered daily intravenously at the indicated doses in saline for a total of 21 days; each experimental value is averaged from at least five animals. Antitumor activity is expressed as T/C % (mean increase of tumor volumes of treated animals divided by the mean increase of tumor volumes of control animals multiplied by 100). The results are shown in Table 7.

TABLE 7

| Group | Dose mg/kg | T/C% |
|---|---|---|
| Placebo | 10 ml/kg | 100 |
| SEQ.ID.NO.19 | 6.0 | 9 |
| SEQ.ID.NO.19 | 0.6 | 12 |
| SEQ.ID.NO.19 | 0.06 | 15 |
| SEQ.ID.NO.19 | 0.006 | 42 |

Example C6

Influence of the Antisense Oligonucleotide Concentration on Clotting Time

The influence of the antisense oligonucleotide concentration on clotting time is determined by using an activated partial thromboplastin time (APTT) method, which is an in vitro diagnostic test designed to identify deficiencies in the intrinsic coagulation pathway (see also K.-H. Altmann et al., Chimia 50 (1996), 168–176), incorporated by reference).

Briefly, 50 µl of human plasma containing a known concentration of oligonucleotide is activated by incubation with 50 µl of bovine-cephalin reagent before coagulation is initiated by the addition of $CaCl_2$ (50 µl, 20 mM). The time taken for coagulation to occur is measured using an Instrumentation Laboratory ACL 300R coagulometer. As the results show, the effect of the antisense oligonucleotide-derivative SEQ.ID.NO.19 on the clotting time is not very pronounced, indicating the beneficial properties of oligonucleotides according to the present invention on non-soecific side effects:

Oligonucleotide SEQ.ID.NO.19: APTT doubled by 123.6 µM.

What is claimed is:

1. A process for preparing a compound of the formula (Ia)

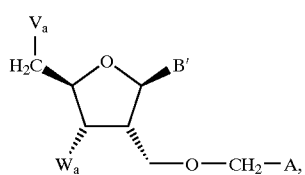

(Ia)

in which

A is a radical of the formula —C(H)($R_3$)—N($R_1$)($R_2$), in which $R_1$ and $R_2$ are independently of each other,

H, $C_1$–$C_{10}$ alkyl, a radical of the formula II

—($CH_2$—$CH_2$—X)$_m$—$R_5$     (II), in which each X is, in each case independently of each other, O or N($R_6$), $R_5$ and $R_6$ mono-$C_1$–$C_{10}$ alkylamino-$C_2$–$C_{10}$ alkyl or N,N-di-$C_1$–$C_{10}$ alkylamino-$C_2$–$C_{10}$ alkyl, and m is an integer from 1 up to and including 3, amino-$C_3$–$C_{10}$ alkyl, N-mono-$C_1$–$C_{10}$ alkylamino-$C_3$–$C_{10}$-alkyl, or N,N-di-$C_1$–$C_{10}$ alkylamino-$C_3$–$C_{10}$ alkyl; or in which —N($R_1$)($R_2$) are together a radical of the formula (III),

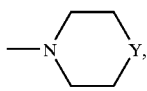

(III)

in which Y is O, S, SO, $SO_2$ or N($R_7$), and $R_7$ is H or —$CH_3$;

$R_3$ is H, —$CH_3$, —$CH_2$—$CH_3$, —$CH_2$OH or —$CH_2$—O—$C_1$–$C_4$ alkyl; or A is a radical of the formula (IVa) or (IVb)

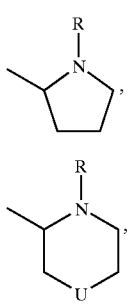

(IVa)

(IVb)

in which R, independently, has the meaning of $R_1$ or $R_2$, and U is O or $CH_2$;
B' is the radical of a nucleic acid base; and
$V_a$ and $W_a$ are, independently of each other, —OH, —$NH_2$ or identically or differently protected hydroxyl or amino groups,
wherein nucleosidic building blocks having, in the radical A, two heteroatoms linked to the same carbon atom are excluded,
and wherein other reactive groups are present in the protected or unprotected state;
wherein said process comprises reacting
(a) a compound of the formula (A)

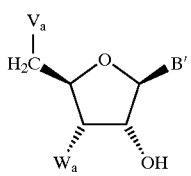

(A)

in which $V_a$ and $W_a$ are, independently of each other, a protected hydroxyl or amino group, and B' is defined as above, with exocyclic amino groups in B' being protected by protecting groups, with a compound of the formula (B)

X—$CH_2$—A (B)

in which X is Cl, Br, I, tosyl-O or mesyl-O, and A is defined as above, with primary and secondary amino groups and primary hydroxyl groups in A being protected by protecting groups; or (b) a compound of the formula (D)

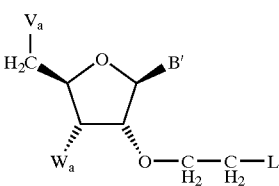

(D)

with a compound of theformula (F)

NH($R_1$) ($R_2$) (F)

wherein functional groups in $R_1$, $R_2$ are protected and L is a leaving group; or
(c) a compound of the formula (D)

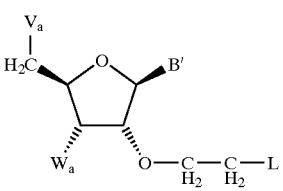

(D)

with an azide and subsequently reducing to provide a compound of the formula (G)

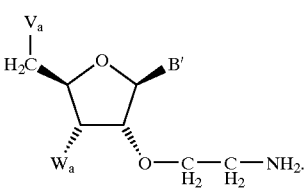

(G)

2. A process of claim 1 wherein a compound of formula (A) is reacted with a compound of formula (B).
3. A process of claim 62 wherein a compound of formula (D) is reacted with a compound of formula (F).
4. A process of c)aim 1 wherein a compound of formula (D) is reacted with a compound of formula (G).

* * * * *

UNITED STATES PATENT AND TRADEMARK OFFICE
CERTIFICATE OF CORRECTION

PATENT NO. : 6,670,468 B1
DATED : December 30, 2003
INVENTOR(S) : Cuenoud et al.

It is certified that error appears in the above-identified patent and that said Letters Patent is hereby corrected as shown below:

Column 80,
Line 43, should read
-- 3. A process of claim 2 wherein a compound of formula --.

Signed and Sealed this

Twenty-third Day of March, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,670,468 B1  
APPLICATION NO. : 09/753943  
DATED : December 30, 2003  
INVENTOR(S) : Cuenoud et al.

Page 1 of 1

It is certified that error appears in the above-identified patent and that said Letters Patent is hereby corrected as shown below:

In the Claims

Column 77, Claim 1 should show the following structure instead of the one printed.

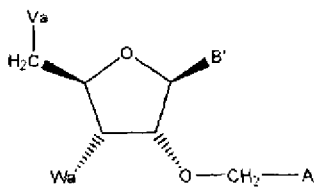

Signed and Sealed this  
Twenty-third Day of April, 2013

Teresa Stanek Rea  
*Acting Director of the United States Patent and Trademark Office*